United States Patent

Chan et al.

[11] Patent Number: 6,013,501
[45] Date of Patent: Jan. 11, 2000

[54] HIPPURICASE GENE

[76] Inventors: Voon Loong Chan, 93 Elmridge Dr., Toronto Ontario M6B 1A6, Canada; Eric Kurt Hani, 37 Greengrove Crescent, Toronto Ontario M3A 1H8, Canada

[21] Appl. No.: 08/853,552

[22] Filed: May 9, 1997

Related U.S. Application Data

[62] Division of application No. 08/485,216, Jun. 7, 1995, Pat. No. 5,695,960, which is a continuation of application No. PCT/CA94/00270, May 13, 1994, which is a continuation-in-part of application No. 08/061,696, May 14, 1993, abandoned.

[51] Int. Cl.[7] .............................. C12N 9/14; C07H 21/04; C07K 1/00
[52] U.S. Cl. .................. 435/195; 435/69.1; 435/252.33; 435/320.1; 536/23.2; 536/23.7; 530/350
[58] Field of Search .................................. 435/195, 69.1, 435/252.33, 320.1; 536/23.2, 23.7; 530/350

[56] References Cited

U.S. PATENT DOCUMENTS

| | | | |
|---|---|---|---|
| 4,785,086 | 11/1988 | Rashtchian | 536/24.32 |
| 5,200,344 | 4/1993 | Blaser et al. | 435/7.32 |

FOREIGN PATENT DOCUMENTS

| | | |
|---|---|---|
| 0350205 | 1/1990 | European Pat. Off. . |
| 0367644 | 5/1990 | European Pat. Off. . |

OTHER PUBLICATIONS

Walker, R.I. et al., Microbiol. Rev. 50(1):81–94, 1986.
Kim, N.W. et al., J. Bacteriol. 174(11):3494–3498, 1992.
Chan, V.L. and Bingham, H.L., Gene 101:51–58, 1991.
Cover, T.L. and Blaser, M.J., Ann. Rev. Med. 40:269–285, 1989.
Kaldor, J. and Speed, B.R., British Medical J. 288:1867–1870, 1984.
Johnsen, K. et al., Acta. Med. Scand. 214:165–168, 1983.
Penner, J.L., Clin. Micro. Rev. 1(2):157–172, 1988.
Cowan, S.T., Int. Bull. Bact. Nom. Tax. 5:97, 1955.
Braunstein, H. et al., Am. J. Clin. Pathol. 51:207, 1969.
Facklam, R.R. et al., Appl. Microbiol. 27:107, 1974.
Kameda, Y. et al., Chem. Pharm. Bull. Tokyo 16(6):1023–1029, 1968.
Röhr M., Monatshefte für Chemie 99:2255–2277, 1968.
Hwang, M. and Ederer, G.M., J. Clin. Microbiol. 1(1):114, 1975.
Edberg, S.C., and Samuels, S., J. Clin. Microbiol. 3:49, 1976.
Ottow, J.C.G., J. Appl. Bacteriol. 37:15, 1974.
Totten, P.A. et al., J. Clin. Microbiol. 25(9):1747–1752.
Bär, W. and Fricke, G., J. Clin. Microbiol. 25(9):1776–1778, 1987.
Wallace, P.L. et al., J. Clin. Microbol. 25(9):1766–1768, 1987.
Romaniuk, P.J. and Trust, T.J., Mol. Cell. Probes 3:133–142, 1989.
Taylor, D.E. and Hiratsuka, K., Mol. Cell. Probes 4:261–271, 1989.
Lior, H. et al., J. Clin. Microbiol. 15:761–768, 1982.
Chang, A.C.Y. et al., Nature 275:617, 1978.
Nichols, B.P. and Yanofsky, C., Meth. In Enzymology 101:155, 1983.
Russel, D.R. et al., Gene 20:231–243, 1982.
Chan et al., Gene 73:185–191, 1988.
Henikoff, S., Gene 28:351–359, 1984.
Hanahan, D., J. Mol. Biol. 166:557–580, 1983.
Sancar, A. et al., J. Bacteriol. 137(1):692–693, 1979.
Sancar, A. et al., J. Mol. Biol. 148:45–62, 1981.
Thirst, M.L., J. Gen. Microbiol. 17:390–395, 1957.
Cacho, J.B. et al., J. Clin. Micro 27:359–360, 1989.
Hébert et al., J. Clin. Micro. 20;138–140, 1984.
Morris, G.K. et al., J. Clin. Micro. 22:714–718, 1985.
Edmonds, P. et al., J. Clin. Micro. 21:936–940, 1985.
Moreau, P. et al., J. Clin. Micro. 27:1514–1517, 1989.
Ziegler, P. and Kutzner, H.J., Zeitschrift für Allg. Mikrobiolgie, 13, 265, 1973.
Hajna, A.A. and Damon, S.R., American J. Hygiene, 19:545, 1934.
Ellis, S. and Walker, B.S., p. 291, 1941.
Röhr, M., Monatshefte für Chemie, 99:2291–2995, 1968.
Hani, E.K. et al., Abstracts of the General Meeting of the American Society for Microbiology, May, 1993, Washington.
On et al. J. Clin. Microbiol. 30(3): 746–749, Mar. 1, 1992.
Miyagawa et al. Agric. Biol. Chem. 49(10): 2881–2886, 1985.

*Primary Examiner*—Robert A. Wax
*Assistant Examiner*—Tekchand Saidha
*Attorney, Agent, or Firm*—Merchant & Gould

[57] ABSTRACT

A nucleic acid molecule having a sequence encoding benzoyl-glycine aminohydrolase, commonly known as hippuricase, of *Camplylobacter jejuni* is provided. Methods are disclosed for detecting *C. jejuni* in a biological sample by determining the presence of hippuricase or a nucleic acid molecule encoding hippuricase in the sample.

3 Claims, 6 Drawing Sheets

FIGURE 1

```
ATG AGT GAC TTT TGG AGA ATA CCT TTG TTA TAC TAT CAT TTA ACC ATG GGT AGT AAA TCT TGG AGT GTT GAT AAA    75
Met Ser Asp Phe Trp Arg Ile Pro Leu Leu Tyr Tyr His Leu Thr Met Gly Ser Lys Ser Trp Ser Val Asp Lys

ACC CAT AGA TTT ACT TTG GGT TTT GTT TAT ATT TTT GCT TTG ATT TTT ATT TCA GCG ATC TTA GCA CAA TTT GTT   150
Thr His Arg Phe Thr Leu Gly Phe Val Tyr Ile Phe Ala Leu Ile Phe Ile Ser Ala Ile Leu Ala Gln Phe Val

TTA CCT AGA AGA GAA AAT TTA TAC AAG GAG AAA AAT AGA TTG AAT TTA ATT CCA GAA TTA ATT CTA GAC TTA CAA GGC   225
Leu Pro Arg Arg Glu Asn Leu Tyr Lys Glu Lys Asn Arg Leu Asn Leu Ile Pro Glu Leu Ile Leu Asp Leu Gln Gly

GAA TTT GAA AAA ATT CGT CAT CAT GAA AAT CCT GGT CTT GAT GAA TTA TGT ACT GCA AAA TTA   300
Glu Phe Glu Lys Ile Arg His His Glu Asn Pro Gly Leu Asp Glu Leu Cys Thr Ala Lys Leu

GTG GCG CAA AAA TTA AAA GAA TTT GGT TAT GAG GTT GTT TAT GAG GAA ATA GGA AAA ACA GGC GTT GTG GGG GTT TTA   375
Val Ala Gln Lys Leu Lys Glu Phe Gly Tyr Glu Val Val Tyr Glu Glu Ile Gly Lys Thr Gly Val Val Gly Val Leu

AAA AGG GGA ATA GCG ATT AAA ATA GGA CTC GTG CTA GTT GCT AAT TGG ATA TTG CCT TTG CAA GAA TGC ACA AAT   450
Lys Arg Gly Ile Ala Ile Lys Ile Gly Leu Val Leu Val Gln Ile Trp Asn Ala Leu Pro Leu Gln Glu Cys Thr Asn

TTG CCT TAT AAA AGC AAA AAA GAA AAT GTA ATG CAT GCT TGC GGT CAT GAT GGA CAT ACT ACT TCT TTA TTG CTT   525
Leu Pro Tyr Lys Ser Lys Lys Glu Asn Val Met His Ala Cys Gly His Asp Gly His Thr Thr Ser Leu Leu Leu

GCT GCA AAG TAT TTA GCA AGT CAG AAT TTT AAT GGC ACT TTA AAT CTT TAT TTT CAA CCT GCT GAA GAG GGT TTG   600
Ala Ala Lys Tyr Leu Ala Ser Gln Asn Phe Asn Gly Thr Leu Asn Leu Tyr Phe Gln Pro Ala Glu Glu Gly Leu

GGT GGT GCT AAG GCA ATG ATA GAA GAT GGA TTG TTT AAA AAT TTT GAT AGT GAT TAT GTT TTT GGA TGG CAC AAT   675
Gly Gly Ala Lys Ala Met Ile Glu Asp Gly Leu Phe Lys Asn Phe Asp Ser Asp Tyr Val Phe Gly Trp His Asn

ATG CCT TTT GGT AGC AAG AAG GAT AAG AAA TTT TAT CTT AAA AAA GGT GCG ATG GCT TCT TCG GAT AGT AGT AGC ATT   750
Met Pro Phe Gly Ser Lys Lys Asp Lys Lys Phe Tyr Leu Lys Lys Gly Ala Met Ala Ser Ser Asp Ser Ser Ile

GAA GTT ATT GGA AGA GGT GGT GGT CAT GCA AGT GCT CAT GCA ATA GAT CCT ATT TAT GCT CCT TCT TTA CTT   825
Glu Val Ile Gly Arg Gly Gly Gly His Ala Ser Ala His Ala Ile Asp Pro Ile Tyr Ala Ala Ser Leu Leu

ATT GTA ACT TTA CAA AGC ATA GTA TCT TGC ATA TCA AAT GTT GAT CCC CAA AAT TCA GCA GTT GTA AGC ATA GGA GCT   900
Ile Val Thr Leu Gln Ser Ile Val Ser Cys Ile Ser Asn Val Asp Pro Gln Asn Ser Ala Val Val Ser Ile Gly Ala

AAT GCT GGA CAT GCT TTT AAT ATC ATT CCA GAT ATT GTA ACG ATT TGT AAA GGT CTT GCA CAG GCT ATT AGA GGA TTA GAT AAT GAA   975
Asn Ala Gly His Ala Phe Asn Ile Ile Pro Asp Ile Val Thr Ile Cys Lys Gly Leu Ala Gln Ala Ile Arg Gly Leu Asp Asn Glu

ACT AGA AAG CTA ACT GAA GAA GTT GTT GCA CCA GTG ACT ATG AAT AAC GAT GAA CTT GCA GCT TTT GCT AGT GAG GTT GCA AAA   1050
Thr Arg Lys Leu Thr Glu Glu Val Val Ala Pro Val Thr Met Asn Asn Asp Glu Leu Ala Ala Phe Ala Ser Glu Val Ala Lys

ATC AAT AAA AAT GTT GCA CCA CCA GTG ACT ATG AAT AAC GAT GAA CTT GCA GCT TTT GCT AGT GAG GTT GCA AAA   1125
Ile Asn Lys Asn Val Ala Pro Val Thr Met Asn Asn Asp Glu Leu Ala Ala Phe Ala Ser Glu Val Ala Lys

GAA TTA TTT GGC GAA AAA AAT TGT GAA TTT AAT CAT CGT CCT CTT ATG ATG GCA AGT GTG GAT TTT TTT TAC   1200
Glu Leu Phe Gly Glu Lys Asn Cys Glu Phe Asn His Arg Pro Leu Met Met Ala Ser Glu Asp Phe Gly Phe Tyr

GAA ATG AAA AAA TGT GCC TAT GCT TTT TTA TTA GAA AAT GAA AAC GAC ATT TAT TTA CAT AAT TCT AGT GTT TTT   1275
Glu Met Lys Lys Cys Ala Tyr Ala Phe Leu Leu Glu Asn Glu Asn Asp Ile Tyr Leu His Asn Ser Ser Val Phe

AAT GAT AAG CTT TTA GCT AGG GCA AGT TAT TAT GCG AAG CTA GCT CTA TTA AAA TAC TTA AAA          1338
Asn Asp Lys Leu Leu Ala Arg Ala Ser Tyr Tyr Ala Lys Leu Ala Leu Leu Lys Tyr Leu Lys
```

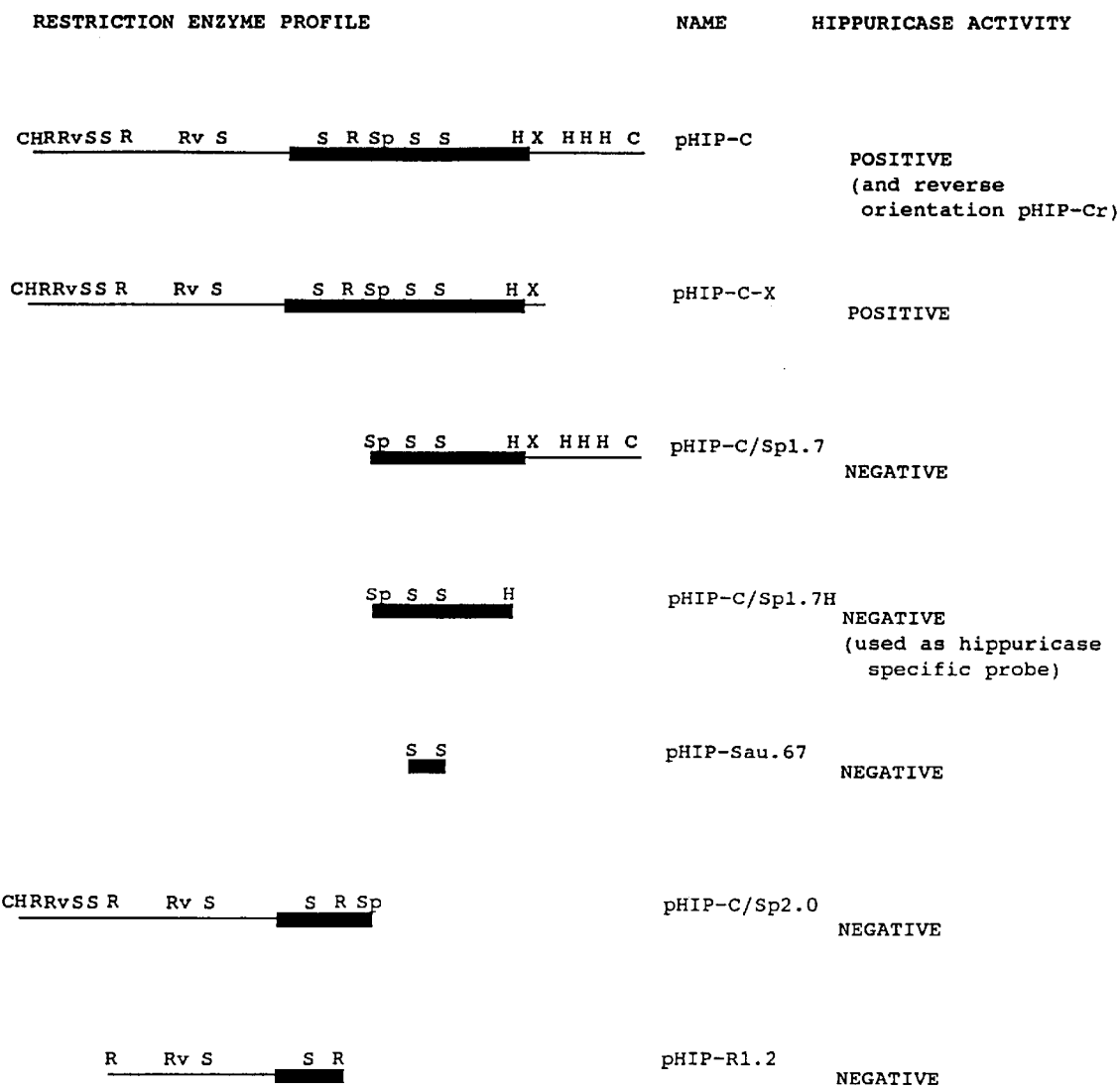
Figure 2. Restriction enzyme map of relevant plamsids. |————|*=0.5 kb.
Legend: C=*Cla*I, H=*Hind*III, R=*Rsa*I, Rv=*Eco*RV, S=*Sau*3A, Sp=*Sph*I, X=*Xba*I.

MAXICELL ANALYSIS OF HIPPURICASE PROTEIN

PROTEIN  
STANDARDS (kD)

E. coli DR1984  
-   +pBR322   +pHIP-O 97  
66  
42  
31

21  
14

HIPPURICASE GENE

This is a Divisional of application Ser. No. 08/485,216, filed Jun. 7, 1995 now U.S. Pat. No. 5,695,960, which is a Continuation of PCT/CA94/00270, filed May 13, 1994, now International Publication No. WO 94/26907, published Nov. 24, 1994, which is a Continuation-In-Part of application Ser. No. 08/061,696, filed May 14, 1993 (abandoned), which application(s) are incorporated herein by reference.

FIELD OF THE INVENTION

The present invention relates to a nucleic acid molecule having a sequence encoding benzoyl-glycine aminohydrolase, commonly known as hippuricase, of *Campylobacter jejuni*, or an oligonucleotide fragment thereof. The nucleic acid molecule of the invention can be used to produce polypeptides having part or all of the primary structural conformation and the enzymatic activity of hippuricase.

The nucleic acid molecule of the invention also permits selection of DNA and amino acid sequences unique to polypeptides having the primary structural confirmation and the enzymatic activity of hippuricase. Novel DNA segments or proteins can thus be constructed which contain the unique DNA and amino acid sequences. The invention also relates to uses of the nucleic acid molecules and the polypeptides of the invention.

BACKGROUND OF THE INVENTION

*Campylobacter jejuni* (*C. jejuni*), a gram-negative microaerophilic bacterium, is a leading cause of bacterial diarrhea and enterocolitis in children and adults in both developing and developed countries (Walker R I et al, Microbiol. Rev. 50 (1): 81–94, 1986; Kim N W et al, J. Bacteriol. 174 (11):3494–3498, 1992; Chan V L and Bingham H L, Gene 101:51–58, 1991). Clinical symptoms of Campylobacter infections range from watery diarrhea to inflammatory dysentery and bloody diarrhea (Cover TL and Blaser N J, Ann. Rev. Ned. 40:269–285, 1989; Walker R I et al, supra). Complications from *C. jejuni* infections have included Guillain-Barré syndrome, a neurological disease which may lead to respiratory paralysis and death, toxic megacolon, acute mesenteric adenitis syndrome, and reactive arthritis (Kaldor J and Speed B R, British Medical J. 288:1867–1870, 1984; Johnson K et al, Acta. Med. Scand. 214:165–168, 1983; Walker R I et al, supra).

*Campylobacter jejuni* is commonly found in surface water, in animals such as cattle, sheep, goats, swine and poultry, in industrial wastes, and in many different types of foods including unpasteurized dairy products. Human pets such as dogs, cats and birds may also be infected with *C. jejuni* and may transmit the bacterium to humans. (Cover T L and Blaser M J, Ann. Rev. Med. 40:269–285, 1989; and Penner, J. L., Clin. Micro. Rev. 1:157–172, 1988).

A number of different strategies have been developed for detecting and identifying *C. jejuni* in food samples, water, and environmental and clinical specimens. *C. jejuni* has been differentiated from other pathogenic camplylobacteria such as *C. coli* and *C. lari*, by its ability to hydrolyze hippurate (Cowan S T, Int. Bull. Bact. Nom. Tax. 5:97, 1955). The enzyme benzoyl-glycine aminohydrolase, commonly known as hippuricase, is responsible for cleaving N-benzoylglycine (hippurate) into benzoic acid and glycine. The enzyme is present in *C. jejuni* and it is either absent or non-functional in other campylobacteria, including *C. coli* and *C. lari*.

Hippuricase activity has been shown in a variety of microorganisms including Actinobacillus, *Aerobacter aerogenes, Aerococcus viridans, Campylobacter jejuni*, certain Enterobacteriaceae, some species in the genera Bacillus, Benekea, Corynebacterium, Listeria, Pediococcus, Pseudomonas, Streptococcus, Mycobacterium, and Nocardia, and in the fungi Fusarium semiticum, and Streptomyces. Hippuricase from Streptococcus (Braunstein H et al., Am. J. Clin. Pathol. 51:207, 1969; Facklam R R et al., Appl. Microbiol. 27:107, 1974), Pseudomonas (Kameda et al., Chem. Pharm. Bull. Tokyo 16:1023, 1968), and Fusarium semicticum (Röhr M., Monatshefte für Chemie 99:2255–2277, 1968), has been partially characterized. The molecular weight has not been determined but it is estimated to be between 70,000 to 100,000. The protein has been shown to be antigenic and antisera has been prepared to the streptococcal enzyme. Only fragmentary evidence on hippuricase is available for other organisms. It has been postulated that hippuricase is used by microorganisms as a mechanism of generating either an amino acid or benzoic acid as a substrate for metabolism.

Methods currently used to detect hippuricase activity in *Campylobacter jejuni* include the standard procedure for streptococci by Hwang and Ederer (Hwang M and Ederer G M, J. Clin. Microbiol. 1:114, 1975; Edberg S C and Samuels S, J. Clin. Microbiol. 3:49, 1976) based on the detection of glycine using a ninhydrin reagent. Hippuricase activity has also been detected through the determination of the second product, benzoic acid (Ottow J C G, J. Appl. Bacteriol. 37:15, 1974; Ayers and Rupp, supra, 1922).

These methods are not adequate to allow accurate detection of *C. jejuni*. For example, *C. coli* may yield weak hippuricase reactions, and *C. jejuni* may give weak or no hippuricase activity (Totten P A et al., J. Clin. Microbiol. 25:1747–1752, 1987). The currently used methods for detecting hippuricase activity are also cumbersome due to the need to culture the organisms prior to testing. Further, nonconventional means such as gas-liquid chromatography must be used to quantitate the hydrolysed benzoic acid product in very weak reactions (Bär W and Fricke G, J. Clin. Microbiol. 25:1776–1778, 1987; Wallace P L et al, J. Clin. Microbiol. 25:3766–1768, 1987).

DNA probes have been developed for detection and identification of *C. jejuni* and other campylobacteria. None of the probes have been fully characterized and the nature of the gene products and their functions are unknown. Romaniuk and Trust (Mol. Cell. Probes 3:133–142, 1989) used partial rRNA sequence information of campylobacteria to develop oligonucleotide probes to 16 S ribosomal RNA. One of these three oligo probes is reported to specifically identify *C. jejuni* and *C. lari*, and the other two are reported to be specific for *C. jejuni*, *C. coli*, and *C. lari*. Barns et al (European Patent Application No. 89306594.6, published on Jan. 10, 1990 as No. 0,350,205) disclose small nucleic acid probes which are reported to be capable of specifically hybridizing to ribosomal RNA of *C. jejuni, C. coli* and *C. laridis* and not to rRNA or rRNA genes of *Pseudomonas aeroginosa, E. coli*, or *Salmonella typhimurium*.

Taylor and Hiratsuka (Mol. Cell. Probes 4:261–271, 1989) developed two DNA probes using cloned *C. jejuni* genomic fragments obtained by screening a lambda gtll library with an antiserum prepared against a 46 kD major outer membrane protein of *C. jejuni* One of the probes (pDT1728) is reported to be *C. jejuni* specific, while the other (pDT1719) is reported to detect *C. jejuni* and *C. coli* but has lower sensitivity for the latter. Rashtchian (U.S. Pat. No. 4,785,086) describes a DNA probe capable of hybridizing to DNA of at least 80% of *C. jejuni* bacteria, as well as DNA in other campylobacteria.

Blaser et al. (U.S. Pat. No. 5,200,344) disclose antigenic compositions, and antibodies against the antigenic compositions, for use in diagnostic testing for *C. jejuni* or *C. coli*. The antigens in the compositions are obtained by acid extraction of surface antigens of *C. jejuni* and/or *C. coli*. The antigenic compositions described by Blaser et al. are not capable of differentiating *C. jejuni* and *C. coli*.

Antibody probes developed for campylobacteria are limited to the serotype antisera used to establish the epidemiological relationship between various Campylobacter isolates. These antibody probes are used only after the isolates have been identified as belonging to the genus by using the conventional methods of biochemical reactions, morphology, cultural and Gram reactions. The serotyping systems of Penner and Lior utilize antibody reactions against heat stable and heat-labile antigens respectively (Penner J L, Clin. Micro. Rev. 1:157–172, 1988; and Lior H et al., J. Clin. Microbiol. 15:761–768, 1982). The thermostable antigens have been proven to be the lipopolysaccharide antigens located in the outer membrane of the organism, and are detected through passive hemagglutination of erythrocytes. The Lior system uses antisera that have been absorbed with thermostable antigens of the homologous serostrain, and detects thermolabile antigens by means of slide agglutination of cell suspensions. The mixture of heat-labile antigens is as yet uncharacterized.

SUMMARY OF THE INVENTION

The present inventors have isolated and identified a nucleotide sequence from *C. jejuni* encoding a protein having hippuricase activity. They have also determined that the sequence is specific for *Campylobacter jejuni* and it is not detectable by DNA hybridization in any other species of Campylobacter. Therefore, the present invention permits the preparation of probes and specific antibodies which will be useful in diagnostic testing to specifically differentiate *C. jejuni* from other campylobacteria. The use of a probe based on the identified hippuricase nucleotide sequence of the invention, or antibodies prepared using a hippuricase protein of the invention, will provide highly specific, sensitive, and rapid means to detect the presence of *C. jejuni* in samples.

The high incidence of *C. jejuni* infections in children and adults in developing and developed countries and the significant costs associated with the treatment of the infections and complications arising therefrom, make it highly desirable to have a rapid and specific test to detect and monitor *C. jejuni* in clinical specimens and in potential sources of the organism. The present invention is important in its ability to specifically detect *C. jejuni* and in not requiring propagation of the organisms.

Accordingly, the present invention provides a purified and isolated nucleic acid molecule comprising a sequence encoding hippuricase of *Campylobacter jejuni*, or an oligonucleotide fragment of the sequence which is unique to hippuricase of *C. jejuni*.

In a preferred embodiment, a purified and isolated nucleic acid molecule is provided having a sequence which encodes hippuricase having an amino acid sequence as shown in FIG. 1 and in the Sequence Listing as SEQ. ID. NO. 1 and No. 2. Most preferably, the purified and isolated nucleic acid molecule comprises (a) a nucleic acid sequence as shown in SEQ ID NO:1 and FIG. 1, wherein T can also be U; (b) nucleic acid sequences complementary to (a); (c) nucleic acid sequences which are at least 85% homologous to (a); or, (d) a fragment of (a) or (b) that is at least 15 bases, preferably 20 to 30 bases, and which will hybridize to (a) or (b) under stringent hybridization conditions.

The nucleic acid molecules of the invention may be inserted into an appropriate expression vector, i.e. a vector which contains the necessary elements for the transcription and translation of the inserted protein-coding sequence. Accordingly, recombinant DNA molecules adapted for transformation of a host cell may be constructed which comprise a nucleic acid molecule of the invention operatively linked to an expression control sequence. A transformant host cell including a recombinant molecule of the invention is also provided. Still further, this invention provides plasmids which comprise the recombinant molecules of the invention.

The present invention further relates to an avirulent strain of *Campylobacter jejuni* comprising an avirulent bacterial carrier strain transformed with a recombinant molecule of the invention, and a vaccine composition comprising a bacterial carrier strain transformed with a recombinant molecule of the invention.

The invention also provides a method of preparing hippuricase utilizing a nucleic acid molecule of the invention. The method comprises culturing a transformant host cell including a recombinant molecule comprising a DNA segment of the invention and an expression control sequence operatively linked to the DNA segment, in a suitable medium until hippuricase is formed and thereafter isolating the hippuricase.

The invention still further provides a purified and isolated polypeptide having part or all of the primary structural confirmation (ie. continuous sequence of amino acid residues) and the enzymatic activity of hippuricase. In a preferred embodiment the polypeptide has an amino acid sequence as shown in FIG. 1 and in the Sequence Listing as SEQ ID NO:1 and NO:2, or a sequence having between 97 and 100 percent homology thereto.

The invention also relates to an antibody specific for an epitope of a polypeptide of the invention, preferably a monoclonal antibody and methods for preparing the antibodies. A method for detecting *C. jejuni* in a sample is provided comprising assaying for hippuricase in the sample. In an embodiment of the invention the method comprises contacting the sample with an antibody of the invention which is capable of being detected after it becomes bound to hippuricase in the sample, and measuring the amount of antibody bound to hippuricase in the sample, or unreacted antibody.

A kit for detecting *Campylobacter jejuni* in a sample comprising an antibody of the invention, preferably a monoclonal antibody and directions for its use is also provided. The kit may also contain reagents which are required for binding of the antibody to hippuricase in the sample.

The nucleic acid molecules of the invention allow those skilled in the art to construct nucleotide probes for use in the detection of nucleotide sequences in samples such as biological, food, or environmental samples. The nucleotide probes may be used to detect nucleotide sequences that encode polypeptides related to or analogous to the hippuricase polypeptides of the invention.

Accordingly, the invention provides a method for detecting the presence of a nucleic acid molecule having a sequence encoding a polypeptide related to or analogous to a polypeptide of the invention, comprising contacting the sample with a nucleotide probe which hybridizes with the nucleic acid molecule, to form a hybridization product under conditions which permit the formation of the hybridization product, and assaying for the hybridization product.

The invention further provides a kit for detecting the presence of a nucleic acid molecule having a sequence encoding a polypeptide related to or analogous to a polypeptide of the invention, comprising a nucleotide probe which hybridizes with the nucleic acid molecule, reagents required for hybridization of the nucleotide probe with the nucleic acid molecule, and directions for its use.

The nucleic acid molecules of the invention also permit the identification and isolation, or synthesis, of nucleotide sequences which may be used as primers to amplify a nucleic acid molecule of the invention, for example in the polymerase chain reaction (PCR).

Accordingly, the invention relates to a method of determining the presence of a nucleic acid molecule having a sequence encoding hippuricase or a predetermined part of hippuricase in a sample, comprising treating the sample with primers which are capable of amplifying the nucleic acid molecule, in a polymerase chain reaction to form amplified sequences, under conditions which permit the formation of amplified sequences, and, assaying for amplified sequences.

The invention further relates to a kit for determining the presence of a nucleic acid molecule having a sequence encoding hippuricase or a predetermined part of hippuricase in a sample, comprising primers which are capable of amplifying the nucleic acid molecule in a polymerase chain reaction to form amplified sequences, reagents required for amplifying the nucleic acid molecule thereof in an amplification reaction, preferably the polymerase chain reaction, means for assaying the amplified sequences, and directions for its use.

The nucleic acid molecules of the invention may also be used to assay for a substance which specifically affects *Campylobacter jejuni*. Accordingly, the invention provides a method for assaying for a substance that affects hippuricase activity comprising providing a polypeptide of the invention, incubating with a substrate of the polypeptide, and a test substance which is suspected of affecting hippuricase, and determining the effect of the substance by comparing to a control. The method may be used, for example, to assay for a substance which affects the growth or pathogenicity of *Campylobacter jejuni*.

BRIEF DESCRIPTION OF DRAWINGS

The invention will now be described in relation to the drawings:

FIG. 1 is the nucleotide sequence of the hippuricase gene of *Campylobacter jejuni*;

FIG. 2 is a restriction map of recombinant plasmid pHIPPO containing the hippuricase gene of *C. Jejuni*;

DETAILED DESCRIPTION OF PREFERRED EMBODIMENTS

Figure 3:
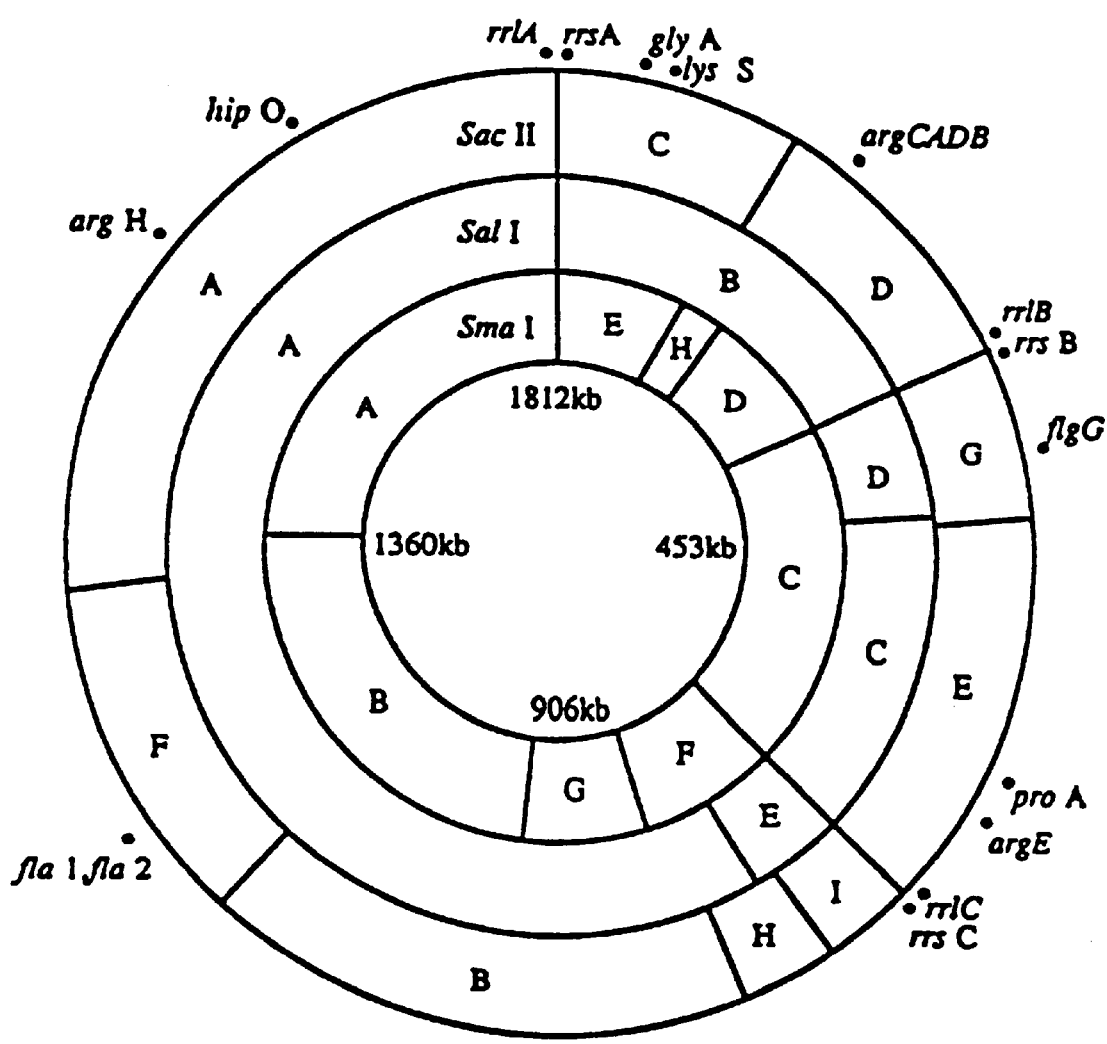
FIG. 3 shows the location of the hippuricase ene on the physical map of *C. jejuni* strain TGH9011.

As hereinbefore mentioned, the present inventors have identified and sequenced a DNA sequence of *C. jejuni* encoding hippuricase. The DNA sequence and deduced amino acid sequence are shown in the Sequence Listing as SEQ ID NO:1 and NO:2.

Nucleic acid molecules of the present invention encoding hippuricase or related or analogous polypeptides may be isolated and sequenced, by selectively amplifying the region of a hippuricase gene, or related or analogous genes, using the polymerase chain reaction method and genomic DNA. It is possible to design synthetic oligonucleotide primers from the sequence shown in the Sequence Listing as SEQ ID NO:1 for use in PCR and for screening genomic libraries. An amplified fragment can be cloned and characterized by DNA sequence analysis. Nucleic acid molecules of the present invention encoding hippuricase may also be constructed by chemical synthesis and enzymatic ligation reactions using procedures known in the art.

It will be appreciated that the invention includes nucleotide or amino acid sequences which have substantial sequence homology with the nucleotide and amino acid sequences shown in the Sequence Listing as SEQ ID NO:1 and NO:2. The term "sequences having substantial sequence homology" means those nucleotide and amino acid sequences which have slight or inconsequential sequence variations from the sequences disclosed in the Sequence Listing as SEQ ID NO:1 and NO:2 i.e. the homologous sequences function in substantially the same manner to produce substantially the same polypeptides as the actual sequences. The variations may be attributable to local mutations or structural modifications. It is expected that a sequence having 85–90% sequence homology with the DNA sequence of the invention will provide a functional hippuricase polypeptide.

Nucleic acid sequences having substantial sequence homology include nucleic acid sequences having at least 85%, preferably at least 90% homology with the nucleic acid sequence as shown in SEQ. ID. NO.:1 and in FIG. 1; and fragments thereof having at least 15 to 30, preferably at least 15 bases, most preferably 20 to 30, which will hybridize to these sequences under stringent hybridization conditions. Stringent hybridization conditions are those which are stringent enough to provide specificity, reduce the number of mismatches and yet are sufficiently flexible to allow formation of stable hybrids at an acceptable rate. Such conditions are known to those skilled in the art and are described, for example, in Sambrook, et al, (1989, Molecular Cloning, A Laboratory Manual, Cold Spring Harbor). By way of example only, stringent hybridization with short nucleotides may be carried out at 5–100 below the $T_m$ using high concentrations of probe such as 0.01–1.0 pmole/ml.

The invention further provides amino acid sequences which have substantial homology with the amino acid sequence shown in SEQ ID NO:2 and in FIG. 1. Substantially homologous sequences include sequences having at least 97% sequence homology.

It will also be appreciated that a double stranded nucleotide sequence comprising a nucleic acid molecule of the invention, hydrogen bonded to a complementary nucleotide base sequence, an RNA made by transcription of this doubled stranded nucleotide sequence, and an antisense strand of a nucleic acid molecule of the invention or an oligonucleotide fragment of the nucleic acid molecule, are contemplated within the scope of the invention.

Analysis of the complete nucleotide and amino acid sequences of the protein of the invention using the procedures of Sambrook et al., 1989, Molecular Cloning, A Laboratory Manual. Cold Spring Harbour Laboratory Press may allow determination of the initiation codon and untranslated sequences of the hippuricase gene. The transcription regulatory sequences of the gene may be determined by analyzing fragments of the DNA for their ability to express a reporter gene such as the bacterial gene lacZ. Primer extension using reverse transcriptase may also be used to determine the initiation site.

In an embodiment of the invention, an antisense sequence of a nucleic acid molecule of the invention is provided. An antisense sequence is constructed by inverting the sequence of a nucleic acid molecule of the invention, relative to its normal presentation for transcription. Preferably, an antisense sequence is constructed by inverting a region preceding the initiation codon or an unconserved region. The antisense sequences may be constructed using chemical synthesis and enzymatic ligation reactions using procedures known in the art.

A number of unique restriction sequences for restriction enzymes are incorporated in the nucleic acid molecule identified in the Sequence Listing as SEQ ID NO:1, and these provide access to nucleotide sequences which code for polypeptides unique to the hippuricase polypeptide of the invention. Nucleotide sequences unique to hippuricase of C. jejuni or isoforms thereof, can also be constructed by chemical synthesis and enzymatic ligation reactions carried out by procedures known in the art.

The nucleic acid molecules of the invention, allow those skilled in the art to construct nucleotide probes for use in the detection of nucleotide sequences in biological materials, such as feces, blood or other bodily fluids or tissues from humans or animals such as mammals and poultry, in foods such as dairy products most particularly milk and poultry, and in environmental samples such as water and industrial wastes.

A nucleotide probe may be labelled with a detectable marker such as a radioactive label which provides for an adequate signal and has sufficient halflife such as 32p, 3 H, 14 C or the like. Other detectable markers which may be used include antigens that are recognized by a specific labelled antibody, fluorescent compounds, enzymes, antibodies specific for a labelled antigen, and chemiluminescent compounds. An appropriate label may be selected having regard to the rate of hybridization and binding of the probe to the nucleotide to be detected and the amount of nucleotide available for hybridization.

The nucleotide probes may be used to detect genes that encode polypeptides related to or analogous to hippuricase of the invention.

Accordingly, the present invention also relates to a method of detecting the presence of nucleic acid molecules encoding a polypeptide related to or analogous to hippuricase of the invention in a sample comprising contacting the sample under hybridization conditions with one or more of the nucleotide probes of the invention labelled with a detectable marker, and determining the degree of hybridization between the nucleic acid molecule in the sample and the nucleotide probes.

Hybridization conditions which may be used in the method of the invention are known in the art and are described for example in Sambrook J, Fritch E F, Maniatis T. In: Molecular Cloning, A Laboratory Manual, 1989. (Nolan C, Ed.), Cold Spring Harbor Laboratory Press, Cold Spring Harbor, N.Y. The hybridization product may be assayed using techniques known in the art. The nucleotide probe may be labelled with a detectable marker as described herein and the hybridization product may be assayed by detecting the detectable marker or the detectable change produced by the detectable marker.

The nucleic acid molecule of the invention also permits the identification and isolation, or synthesis of nucleotide sequences which may be used as primers to amplify a nucleic acid molecule of the invention, for example in the polymerase chain reaction (PCR) which is discussed in more detail below. The primers may be used to amplify the genomic DNA of other bacterial species known to possess hippuricase activity such as *Bacillus subtilis* and *Streptococcus faecalis*. The PCR amplified sequences can be examined to determine the relationship between the various hippuricase genes.

The length and bases of the primers for use in the PCR are selected so that they will hybridize to different strands of the desired sequence and at relative positions along the sequence such that an extension product synthesized from one primer when it is separated from its template can serve as a template for extension of the other primer into a nucleic acid of defined length.

Primers which may be used in the invention are oligonucleotides i.e. molecules containing two or more deoxyribonucleotides of the nucleic acid molecule of the invention which occur naturally as in a purified restriction endonuclease digest or are produced synthetically using techniques known in the art such as for example phosphotriester and phosphodiester methods (See Good et al Nucl. Acid Res 4:2157, 1977) or automated techniques (See for example, Conolly, B. A. Nucleic Acids Res. 15:15 (7): 3131, 1987). The primers are capable of acting as a point of initiation of synthesis when placed under conditions which permit the synthesis of a primer extension product which is complementary to the DNA sequence of the invention i.e. in the presence of nucleotide substrates, an agent for polymerization such as DNA polymerase and at suitable temperature and pH. Preferably, the primers are sequences that do not form secondary structures by base pairing with other copies of the primer or sequences that form a hair pin configuration. The primer may be single or double-stranded. When the primer is double-stranded it may be treated to separate its strands before using to prepare amplification products. The primer preferably contains between about 7 and 25 nucleotides.

The primers may be labelled with detectable markers which allow for detection of the amplified products. Suitable detectable markers are radioactive markers such as P-32, S-35, I-125, and H-3, luminescent markers such as chemiluminescent markers, preferably luminol, and fluorescent markers, preferably dansyl chloride, fluorcein-5-isothiocyanate, and 4-fluor-7-nitrobenz-2-axa-1,3 diazole, enzyme markers such as horseradish peroxidase, alkaline phosphatase, β-galactosidase, acetylcholinesterase, or biotin.

It will be appreciated that the primers may contain non-complementary sequences provided that a sufficient amount of the primer contains a sequence which is complementary to a nucleic acid molecule of the invention or oligonucleotide sequence thereof, which is to be amplified. Restriction site linkers may also be incorporated into the primers allowing for digestion of the amplified products with the appropriate restriction enzymes facilitating cloning and sequencing of the amplified product.

In an embodiment of the invention a method of determining the presence of a nucleic acid molecule having a sequence encoding hippuricase or a predetermined oligonucleotide fragment thereof in a sample, is provided comprising treating the sample with primers which are capable of amplifying the nucleic acid molecule or the predetermined oligonucleotide fragment thereof in a polymerase chain reaction to form amplified sequences, under conditions which permit the formation of amplified sequences and, assaying for amplified sequences.

The polymerase chain reaction refers to a process for amplifying a target nucleic acid sequence as generally described in Innis et al, Academic Press, 1990 in Mullis el al., U.S. Pat. No. 4,863,195 and Mullis, U.S. Pat. No. 4,683,202 which are incorporated herein by reference. Conditions for amplifying a nucleic acid template are described in M. A. Innis and D. H. Gelfand, PCR Protocols, A Guide to Methods and Applications M. A. Innis, D. H. Gelfand, J. J. Sninsky and T. J. White eds, pp3–12, Academic Press 1989, which is aleo incorporated herein by reference.

The process described by Mullis amplifies any desired specific nucleotide sequence contained in a nucleic acid or mixture thereof. The process involves treating separate complementary strands of the nucleotide sequence to be amplified with two oligonucleotide primers which are extended under suitable conditions to form complementary primer extension products which act as templates for synthesizing the nucleotide sequence. The primers are selected so that they are sufficiently complementary to different strands of each specific nucleotide sequence to be amplified. The steps of the PCR reaction may be carried out sequentially or simultaneously and the steps may be repeated until the desired level of amplification is obtained.

The amplified products can be isolated and distinguished based on their respective sizes using techniques known in the art. For example, after amplification, the DNA sample can be separated on an agarose gel and visualized, after staining with ethidium bromide, under ultra violet (W) light. DNA may be amplified to a desired level and a further extension reaction may be performed to incorporate nucleotide derivatives having detectable markers such as radioactive labelled or biotin labelled nucleoside triphosphates. The primers may also be labelled with detectable markers. The detectable markers may be analyzed by restriction and electrophoretic separation or other techniques known in the art.

The conditions which may be employed in the methods of the invention using PCR are those which permit hybridization and amplification reactions to proceed in the presence of DNA in a sample and appropriate complementary hybridization primers. Conditions suitable for the polymerase chain reaction are generally known in the art. For example, see M. A. Innis and D. H. Gelfand, PCR Protocols, A guide to Methods and Applications M. A. Innis, D. H. Gelfand, J. J. Sninsky and T. J. White eds, pp3–12, Academic Press 1989, which is incorporated herein by reference. Preferably, the PCR utilizes polymerase obtained from the thermophilic bacterium Thermus aquatics (Taq polymerase, GeneAmp Kit, Perkin Elmer Cetus) or other thermostable polymerase may be used to amplify DNA template strands.

It will be appreciated that other techniques such as the Ligase Chain Reaction (LCR) and NASBA may be used to amplify a nucleic acid molecule of the invention. In LCR, two primers which hybridize adjacent to each other on the target strand are ligated in the presence of the target strand to produce a complementary strand (Barney in "PCR Methods and Applications", August 1991, Vol.1 (1), page 5, and European Published Application No. 0320308, published Jun. 14, 1989). NASBA is a continuous amplification method using two primers, one incorporating a promoter sequence recognized by an RNA polymerase and the second derived from the complementary sequence of the target sequence to the first primer (U.S. Ser. No. 5,130,238 to Malek).

A nucleic acid molecule of the present invention may be incorporated in a known manner into a recombinant molecule which ensures good expression of the hippuricase polypeptide or part thereof. In general, a recombinant molecule of the invention contains a nucleic acid molecule of the invention and a suitable transcriptional or translational regulatory element operatively linked to the nucleic acid molecule. Suitable regulatory elements may be derived from a variety of sources, including bacterial, fungal, viral, mammalian or insect genes. Selection of appropriate regulatory elements is dependent on the host cell chosen, and may be readily accomplished by one of ordinary skill in the art. Examples of regulatory elements include: a transcriptional promoter and enhancer or RNA polymerase binding sequence, a ribosomal binding sequence, including a translation initiation signal. Additionally, depending on the host cell chosen and the vector employed, other genetic elements, such as an origin of replication, additional DNA restriction sites, enhancers, sequences conferring inducibility of transcription, and selectable markers, may be incorporated into the expression vector. Preferably the regulatory sequences of the hippuricase gene are used as the regulatory elements in a recombinant molecule of the invention. The regulatory sequences of the hippuricase gene may be isolated as described above. A nucleic acid molecule of the invention, may be incorporated into a plasmid vector. The plasmid vectors may be designed to facilitate subsequent purification of the encoded protein or parts thereof by affinity chromatography. For example, gene fusion systems such as the glutathione S-transferase gene fusion system may be utilized.

The hippuricase polypeptide or isoforms or parts thereof, may be obtained by expression in a suitable host cell using techniques known in the art. Suitable host cells include prokaryotic or eukaryotic organisms or cell lines, for example bacterial, mammalian, yeast, or other fungi, viral, plant or insect cells. Methods for transforming or transfecting cells to express foreign DNA are well known in the art (See for example, Itakura et al., U.S. Pat. No. 4,704,362; Hinnen et al., PNAS USA 75:1929–1933, 1978; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddal et al., U.S. Pat. No. 4,766,075; and Sambrook et al Molecular Cloning: A Laboratory Manual 2nd Ed, Cold Spring Harbor Laboratory Press, 1989, all of which are incorporated herein by reference).

Bacterial hosts suitable for carrying out the present invention include *E. coli* as well as many other bacterial species well known to one of ordinary skill in the art. Representative examples of bacterial host cells include *E. coli*, Streptococcus, Campylobacter, and *Bacillus subtilus*.

Bacterial expression vectors preferably comprise a promoter which functions in the host cell, one or more selectable phenotypic markers, and a bacterial origin of replication. Representative promoters include the β-lactamase (pencillinase) and lactose promoter system (see Chang et al., Nature 275:615, 1978), the trp promoter (Nichols and Yanofsky, Meth. in Enzymology 101:155, 1983) and the tac promoter (Russel el al., Gene 20: 231, 1982). Examples of selectable markers are various antibiotic resistance markers such as the kanamycin or ampicillin resistance genes. Nany plasmids suitable for transforming host cells are well known in the art, including pBR322 (see Bolivar et al., Gene 2:95, 1977), the pUC plasmids pUC18, pUC19, pUC118, pUC119 (see Messing, Neth. in Enzymology 101:20–77, 1983 and Vieira and Messing, Gene 19:259–268, 1982), and pNH8A, pNH16a, pNH18a and pBluescript M13 (Stratagene, La Jolla, Calif.).

Yeast and fungi host cells suitable for carrying out the present invention include, among others Saccharomyces cerevisiae, the genera Pinchi or Kluyveromyces and various species of the genus Aspergillus. Suitable expression vectors for yeast and fungi include, among others, YCp50 (ATCC No. 37419) for yeast, and amdS cloning vector pV3 (Turnbull, Bio/Technology 7:169, 1989). Protocols for the transformation of yeast are also well known to those of ordinary skill in the art. For example, transformation may be readily accomplished either by preparation of spheroplasts of yeast with DNA (see Hinnen et al., PNAS USA 75:1929, 1978) or by treatment with alkaline salts such as LiCl (see Itoh et al., J. Bacteriology 153:163, 1983). Transformation of fungi may also be carried out sing polyethylene glycol as described by Cullen et al. (Bio/Technology 5:369, 1987).

The polypeptides of the invention may be prepared by culturing the host/vector systems described above, in order to express the recombinant polypeptides. Recombinantly produced hippuricase or parts thereof, may be further purified using techniques known in the art such as commercially available protein concentration systems, by salting out the protein followed by dialysis, by affinity chromatography, or using anion or cation exchange resins.

In a preferred embodiment, a nucleic acid molecule of the invention may be cloned into a glutathione S-transferase (GST) gene fusion system for example the pGEX-1 T, pGEX-2T and pGEX-3X of Pharmacia. The fused gene may contain a strong tac promoter, inducible to a high level of expression by IPTG, as a regulatory element. Thrombin or factor Xa cleavage sites may be present which allow proteolytic cleavage of the desired polypeptide from the fusion product. The glutathione S-transferase-hippuricase fusion protein may be easily purified using a glutathione sepharose 4B column, for example from Pharmacia. The 26 kd glutathione S-transferase polypeptide can be cleaved by thrombin (pGEX-1 or pGEX-2T) or factor Xa (pGEX-3X) and resolved from the hippuricase polypeptide using the same affinity column. Additional chromatographic steps can be included if necessary, for example Sephadex or DEAE cellulose. The two enzymes may be monitored by protein and enzymatic assays and purity may be confirmed using SDS-PAGE.

The hippuricase protein or parts thereof may also be prepared by chemical synthesis using techniques well known in the chemistry of proteins such as solid phase synthesis (Merrifield, 1964, J. Am. Chem. Assoc. 85:2149–2154) or synthesis in homogenous solution (Houbenweyl, 1987, Methods of Organic Chemistry, ed. E. Wansch, Vol. 15 I and II, Thieme, Stuttgart).

Within the context of the present invention, hippuricase polypeptide may include various structural forms of the primary protein which retain biological activity. For example, hippuricase polypeptide may be in the form of acidic or basic salts or in neutral form. In addition, individual amino acid residues may be modified by oxidation or reduction. Furthermore, various substitutions, deletions or additions may be made to the amino acid or nucleic acid sequences, the net effect being that biological activity of hippuricase is retained. Due to code degeneracy, for, example, there may be considerable variation in nucleotide sequences encoding the same amino acid.

Mutations in nucleotide sequences constructed for expression of derivatives of hippuricase polypeptide must preserve the reading frame phase of the coding sequences. Furthermore, the mutations will preferably not create complementary regions that could hybridize to produce secondary mRNA structures, such as loops or hairpins, which could adversely affect translation of the receptor mRNA.

Mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Alternatively, oligonucleotide-directed site specific mutagenesis procedures may be employed to provide an altered gene having particular codons altered according to the substitution, deletion, or insertion required. Deletion or truncation of hippuricase may also be constructed by utilizing convenient restriction endonuclease sites adjacent to the desired deletion. Subsequent to restriction, overhangs may be filled in, and the DNA relegated. Exemplary methods of making the alterations set forth above are disclosed by Sambrook et al (Molecular Cloning: A Laboratory Manual, 2d Ed., Cold Spring Harbor Laboratory Press, 1989).

The hippuricase polypeptide of the invention may be expressed in an avirulent bacterial carrier strain such as Salmonella and Shigella strains. Accordingly, in a further aspect of the invention an avirulent strain of a C. jejuni is provided comprising an avirulent bacterial carrier strain transformed with a recombinant molecule of the invention. The avirulent strain may provide the basis for a vaccine composition which may be useful for effecting immunity against diseases caused by C. jejuni. The invention therefore also provides a vaccine composition comprising a bacterial carrier strain transformed with a recombinant molecule of the invention. The vaccine composition may be useful in effecting immunity against diseases caused by C. jejuni.

The vaccine compositions can be prepared by per se known methods for the preparation of pharmaceutically acceptable vaccines which can be administered to patients. The vaccine composition may be in an oral or injectable form and may include pharmaceutically acceptable vehicles. On this basis, the vaccine compositions include, albeit not exclusively, solutions of the bacterial carrier strain transformed with a recombinant molecule of the invention in association with one or more pharmaceutically acceptable vehicles or diluents, and contained in buffered solutions with a suitable pH and iso-osmotic with the physiological fluids. Suitable pharmaceutically acceptable vehicles or diluents are described, for example, in Remington's Pharmaceutical Sciences (Mack Publishing Company, Easton, Pa., U.S.A., 1985).

The hippuricase protein of the invention or parts thereof, may be used to prepare antibodies. "Antibodies" used herein are understood to include polyclonal antibodies, monoclonal antibodies, antibody fragments (e.g., Fab' and F(ab')2 ) and recombinantly produced partners. Antibodies may be prepared which bind a distinct epitope in an unconserved region of the protein; for example the nucleotide binding folds.

Conventional methods can be used to prepare the antibodies. Monoclonal antibodies may be readily generated using conventional techniques (see U.S. Pat. Nos. RE 32,011, 4,902,614, 4,543,439, and 4,411,993 which are incorporated herein by reference; see also "Monoclonal Antibodies, Hybridomas: A New Dimension in Biological Analyses", Plenum Press, Kennett, McKearn, and Bechtol (eds.), Cold Spring Harbor Laboratory Press, 1988, and Goding, J. W., Monoclonal Antibodies: Principles and Practice, 2nd Ed., Academic Press, London, 1986 which are also incorporated herein by reference).

Briefly, in one embodiment a subject animal such as a rat or mouse is injected with a polypeptide of the invention. The polypeptide may be admixed with an adjuvant such as Freund's complete or incomplete adjuvant in order to increase the resultant immune response. Between one and three weeks after the initial immunization the animal may be reimmunized with another booster immunization, and tested for reactivity to hippuricase using assays described above. Once the animal's reactivity to hippuricase has plateaued, the animal is sacrificed, and organs which contain large numbers of B cells such as the spleen and lymph nodes are harvested.

Cells which are obtained from immunized animals may be immortalized by transfection with a virus such as the Epstein bar virus (EBV) (see Glasky and Reading, Hybridoma 8 (4):377–389, 1989). Alternatively, within a preferred embodiment, the harvested spleen and/or lymph node cell suspensions are fused with a suitable myeloma cell in order to create a "hybridoma" which secretes monoclonal antibody. Suitable myeloma lines include, for example, NS-1 (ATCC No. TIB 18), and P3X63-Ag 8.653 (ATCC No. CRL 1580).

Following the fusion, the cells may be placed in culture plates containing a suitable medium, such as RPMI 1640, or DMEM (Dulbecco's Modified Eagles Medium) (JRH Biosciences, Lenexa, Kans.), as well as additional ingredients, such as Fetal Bovine Serum (FBS, i.e., from Hyclone, Logan, Utah, or JRH Biosciences). Additionally, the medium should contain a reagent which selectively allows for the growth of fused spleen and myeloma cells such as HAT (hypoxanthine, aminopterin, and thymidine) (Sigma Chemical Co., St. Louis, Mo.). After about seven days, the resulting fused cells or hybridomas may be screened in order to determine the presence of antibodies which are reactive against hippuricase. A wide variety of assays may be utilized to determine the presence of antibodies which are reactive against hippuricase, including for example Countercurrent Immuno-Electrophoresis, Radioimmunoassays, Radioimmunoprecipitations, Enzyme-Linked Immunosorbent Assays (ELISA), DOT Blot assays, Inhibition or Competition Assays, and sandwich assays (see U.S. Pat. Nos. 4,376,101 and 4,486,530; see also Antibodies: A Laboratory Manual, Harlow and Lane (eds.), Cold Spring Harbor Laboratory Press, 1988). Following several clonal dilutions and reassays, a hybridoma producing antibodies reactive against a polypeptide of the invention may be isolated.

Other techniques may also be utilized to construct monoclonal antibodies (see William D. Huse et al., "Generation of a Large Combinational Library of the Immunoglobulin Repertoire in Phage Lambda," Science 246:1275–1281, December 1989; see also L. Sastry et al., "Cloning of the Immunological Repertoire in Escherichia coli for Generation of Monoclonal Catalytic Antibodies: Construction of a Heavy Chain Variable Region-Specific cDNA Library," Proc. Natl. Acad. Sci. USA 86:5728–5732, August 1989; see also Michelle Alting-Mees et al., "Monoclonal Antibody Expression Libraries: A Rapid Alternative to Hybridomas," Strategies in Molecular Biology 3:1–9, January 1990; these references describe a commercial system available from Stratacyte, La Jolla, Calif., which enables the production of antibodies through recombinant techniques). Briefly, mRNA is isolated from a Bell cell population, and utilized to create heavy and light chain immunoglobulin cDNA expression libraries in the yImmunoZap(H) and yImmunoZap(L) vectors. These vectors may be screened individually or co-expressed to form Fab fragments or antibodies (see Huse et al., supra; see also Sastry et al., supra). Positive plaques may subsequently be converted to a non-lytic plasmid which allows high level expression of monoclonal antibody fragments from E. coli.

Similarly, binding partners may also be constructed utilizing recombinant DNA techniques to incorporate the variable regions of a gene which encodes a specifically binding antibody. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources. Stratacyte (La Jolla, Calif.) sells primers for mouse and human variable regions including among others, primers for $V_{Ha}$, $V_{Hb}$, $V_{Hd}$, $C^{H1}$, $V^L$ and CL regions. These primers may be utilized to amplify heavy or light chain variable regions, which may then be inserted into vectors such as ImmunoZAP™ H or ImmunoZAP™ L (Stratacyte), respectively. These vectors may then be introduced into E. coli for expression. Mouse-human chimeric monoclonal antibodies may be constructed using the DNA sequences of the invention in the method described by Hirofumi Hamada et al., Cancer Research 50, 3167–3171, 1991 and Yasuhiko Nishiola et al., Jpn. J. Cancer Res. 83, 644–649, 1192.

Utilizing these techniques, large amounts of a single-chain protein containing a fusion of the VH and VL domains may be produced (see Bird et al., Science 242:423426, 1988). In addition, such techniques may be utilized to change a "murine" antibody to a "human" antibody, without altering the binding specificity of the antibody.

Once suitable antibodies or binding partners have been obtained, they may be isolated or purified by many techniques well known to those of ordinary skill in the art (see Antibodies: A -Laboratory Manual, Harlow and Lane (eds.), Cold Spring Harbor Laboratory Press, 1988). Suitable techniques including peptide or protein affinity columns, HPLC or RP-HPLC, purification on protein A or protein G columns, or any combination of these techniques.

Another method of generating high-affinity antihippuricase antibodies is the recombinant phage antibody system developed by Clackson et al, Nature 352:624–628 (1991), which depends upon the ability of M13 phage to exhibit functional antibody fragments as fusion proteins on their surface. Reagents and the phage vector pCANTAB 5 are commercially available from Pharmacia. The antibodyencoding gene is a recombinant gene consisting of the variable heavy and light encoding sequence separated by a linker sequence. The recombinant gene, SCFV (single-chain fragment variable) is cloned into a phagemid and expressed at the tip of the phage gene 3 protein in the presence of helper phage K07. The antigen-reactive recombinant phage can be detected with anti-M13 antibody conjugated to horseradish peroxidase. Recombinant phages which produce SCFV polypeptides with high affinity for the C. jejuni hippuricase can be enriched by passage over hippuricase affinity columns or by panning the recombinant phage library against the purified C. jejuni hippuricase. Pooled or specific clones of recombinant phages which produce SCFV polypeptides which react specifically with C. jejuni hippuricase may be used in developing the immunoprobe. A specific recombinant phage is anglogous to specific monoclonal antibody.

Polyclonal antibodies may be readily generated by one of ordinary skill in the art from a variety of warm-blooded animals such as horses, cows, various fowl, rabbits, mice, or rats. Briefly, a polypeptide of the invention is utilized to immunize the animal through intraperitoneal, intramuscular, intraocular, or subcutaneous injections. An adjuvant such as Freund's complete or incomplete adjuvant may also be employed. Following several booster immunizations, samples of serum are collected and tested for reactivity to hippuricase. Particularly preferred polyclonal antisera will give a signal on one of these assays that is at least three times greater than background. Once the titer of the animal has reached a plateau in terms of its reactivity to hippuricase, larger quantities of antisera may be readily obtained either by weekly bleedings, or by exsanguinating the animal.

High titre antisera against hippuricase may be developed in rabbits by immunization with the purified hippuricase polypeptide of the invention or with different hydrophilic domains of the C. jejuni hippuricase. Hippuricase-specific antibody may be purified using DEAE cellulose and affinity columns (See Juranka, P. and VL 15 Chan, J. Biol. Chem. 260 (12):7738–7743, 1985). The specificity of the antibodies can be tested by reacting with hippuricase from C. jejuni and other microorganisms that have been shown to possess hippuricase activity.

In a preferred embodiment, a high-titre anti-enzyme serum is produced by injecting the purified polypeptide in Tris/saline buffer and Freund's complete adjuvant (initial injection only) subcutaneously into the back of New Zealand White Rabbits, and once a week for 2 additional weeks with Freund's incomplete adjuvant. Booster injections with Freund's incomplete adjuvant are given 4 weeks later and the rabbits are bled 1 week after the booster through a small incision of the major vein located in the ears. The procedure is repeated several times with each rabbit.

The polyclonal, monoclonal or chimeric monoclonal antibodies may be used to detect hippuricase, parts thereof or closely related isoforms in various samples, for example they may be used in an ELISA, radioimmunoassay or histochemical tests. Thus, the antibodies may be used to quantify the amount of hippuricase, parts thereof or closely related isoforms in a sample in order to diagnose C. jejuni infections. Using methods described hereinbefore, polyclonal or monoclonal antibodies may be raised to nonconserved regions of hippuricase and used to distinguish hippuricase from closely related isoforms and other proteins that share a common conserved epitope.

The polyclonal or monoclonal antibodies may be labelled with a detectable marker including various enzymes, fluorescent materials, luminescent materials and 35 radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include S-35, Cu-64, Ga-67, Zr-89, Ru-97, Tc-99m, Rh-105, Pd-109, In-1111, I-123, I-125, I131, Re-186, Au-198, Au-199, Pb-203, At-211, Pb-212 and Bi-212. The antibodies may also be labelled or conjugated to one partner of a ligand binding pair. Representative examples include avidin-biotin and riboflavin-riboflavin binding protein.

Methods for conjugating or labelling the antibodies discussed above with the representative labels set forth above may be readily accomplished using conventional techniques such as described in U.S. Pat. No. 4,744,981 (Trichothecene Antibody); U.S. Pat. No. 5,106,951 (Antibody Conjugate); U.S. Pat. No. 4,018,884 (Fluorengenic Materials and Labelling Techniques); U.S. 20 Pat. No. 4,897,255 (Metal Radionucleotide Labeled Proteins for Diagnosis and Therapy); U.S. Pat. No. 4,988,496 (Metal Radionuclide Chelating Compounds for Improved Chelation Kinetics); Inman, Methods in Enzymology, Vol. 34, Affinity Techniques, Enzyme Purification; Part B, Jacoby and Wichek (eds) Academic Press, New York, p. 30, 1974; and Wilchek and Bayer, The Avidin-Biotin Complex in Bioanalytical Applications Anal. Biochem. 171:1–32, 1988.

Any sample suspected of containing C. jejuni may be tested for the presence or absence of hippuricase in accordance with the methods set forth herein. Samples which may be tested include bodily materials such as blood, serum, urine, tears, saliva, feces, tissues and the like. Both medical and veterinary applications are contemplated. In addition to human samples, samples may be taken from poultry or mammals such as non-human primates, horses, swine etc. Further, water and food samples and other environmental samples and industrial wastes may be tested.

Before testing a sample in accordance with the methods described herein, the sample may be concentrated using techniques known in the art, such as centrifugation and filtration. For example, a water sample of from 1 to 100 ml may be subjected to centrifugation at 10,000×g for about 15 minutes and the cells can be transferred to an Eppendorf tube and resedimented at 10,000×g for 5 minutes. Alternatively, the cells in the sample may be concentrated by filtration with a 0.4 μm pore size teflon filter and resuspending in water by vortexing. The cells may be lysed with equal volumes of 2×SDS gel-loading buffer (Sambrook et al, 1989, supra) and boiled for 5 minutes. For the hybridization and/or PCR-based methods described herein, nucleic acids may be extracted from cell extracts of the test sample using techniques known in the art.

In a method of the invention a predetermined amount of a sample or concentrated sample is mixed with antibody or labelled antibody. The amount of antibody used in the process is dependent upon the labelling agent chosen. The resulting hippuricase bound to antibody or labelled antibody may be isolated by conventional isolation techniques, for example, salting out, chromatography, electrophoresis, gel filtration, fractionation, absorption, polyacrylamide gel electrophoresis, agglutination, or combinations thereof.

The sample or antibody may be insolubilized, for example, the sample or antibody can be reacted using known methods with a suitable carrier. Examples of suitable carriers are Sepharose or agarose beads. When an insolubilized sample or antibody is used the hippuricase bound to antibody or unreacted antibody is isolated by washing. For example, when the sample is blotted onto a nitrocellulose membrane, the antibody bound to hippuricase is separated from the unreacted antibody by washing with a buffer, for example, phosphate buffered saline (PBS) with bovine serum albumin (BSA).

When labelled antibody is used, the presence of C. jejuni can be determined by measuring the amount of labelled antibody bound to hippuricase in the sample or of the unreacted labelled antibody. The appropriate method of measuring the labelled material is dependent upon the labelling agent. For example, if the labelling agent is an enzyme, the presence of C. jejuni can be determined by measuring the enzymatic activity using a proper enzyme substrate for colorimetric, luminescent or fluorescent systems. If the labelling agent is a fluorescent material, the presence of C. jejuni can be determined by measuring fluorescence intensity, and if the labelling agent is a radioactive material, the presence of C. jejuni can be determined by measuring the radioactivity.

When unlabelled antibody is used in the method of the invention, the presence of C. jejuni can be determined by measuring the amount of antibody bound to C. jejuni using substances that interact specifically with the antibody to cause agglutination or precipitation. In particular, labelled antibody against hippuricase specific antibody, can be added to the reaction mixture. The presence of C. jejuni can be determined by a suitable method from among the already described techniques depending on the type of labelling agent. The antibody against hippuricase specific antibody can be prepared and labelled by conventional procedures known in the art which have been described herein. The antibody against hippuricase specific antibody may be a species specific anti-immunoglobulin antibody or monoclonal antibody, for example, goat anti-rabbit antibody may be used to detect rabbit anti-hippuricase antibody.

In an embodiment of the invention the antibody of the invention is used as the basis of an enzyme-linked immunosorbent assay for the detection of hippuricase. The immunoassay involves coating a solid support with polyvalent rabbit anti-hippuricase antibody, which would capture hippuricase protein present in samples containing C. jejuni. The captured hippuricase antigen can be detected using a biotinylated affinity purified hippuricase specific antibody. The hippuricase-antibody-biotin complex can be readily detected colorimetrically using a streptavidin-alkaline phosphatase colour development system. The immunoassay may be in the form of a dip-stick.

A polypeptide of the invention may also be used to assay for a substance which specifically affects Campylobacter jejuni. Accordingly, the invention provides a method for assaying for a substance that affects hippuricase activity comprising providing a polypeptide of the invention, incubating with a substrate of the polypeptide, and a test substance which is suspected of affecting hippuricase, and determining the effect of the substance by comparing to a control. The method may be used, for example, to assay for a substance which affects the growth or the pathogenesis of Campylobacter jejuni. Representative substrates which may be used in the assay are hippurate, N-Benzoyl-DL-alanine, Nα-Benzoyl-L-arginine, N-benzoyl-L-glutamic acid, N-Benzoyl-L-glycine, Nα-Benzoyl-L-histidine, N-Benzoyl-DL-leucine, N-Benzoyl-DL-methionine, N-Benzoyl-DL-phenylalanine, N-Benzoyl-L-threonine and N-Benzoyl-DL-valine.

The reagents suitable for applying the methods of the invention may be packaged into convenient kits providing the necessary materials, packaged into suitable containers. Such kits may include all the reagents required to detect C. jejuni in a sample by means of the methods described herein, and optionally suitable supports useful in performing the methods of the invention. In one embodiment of the invention the kit contains a nucleotide probe which hybridizes with a nucleic acid molecule of the invention, reagents required for hybridization of the nucleotide probe with the nucleic acid molecule, and directions for its use. In another embodiment of the invention the kit includes antibodies of the invention and reagents required for binding of the antibody to C. jejuni hippuricase in a sample. In still another embodiment of the invention, the kit includes primers which are capable of amplifying a nucleic acid molecule of the invention or a predetermined oligonucleotide fragment thereof, all the reagents required to produce the amplified nucleic acid molecule or predetermined fragment thereof in the polymerase chain reaction, and means for assaying the amplified sequences. The methods and kits of the present invention have many practical applications. For example, the methods and kits of the present invention may be used to detect C. jejuni in any medical or veterinary sample including bodily materials such as blood, serum, urine, tears, saliva, feces, tissues and the like, samples from poultry or mammals such as non-human primates, horses, swine etc, and water and food samples, other environmental samples and industrial wastes.

The invention will be more fully understood by reference to the following examples. However, the examples are merely intended to illustrate embodiments of the invention and are not to be construed to limit the scope of the invention.

EXAMPLES

Materials and methods used in the examples described herein include the following:

Bacterial strains and plasmids. Campylobacter jejuni ATCC43431 (strain TGH9011, serotype reference strain for 0:3) was obtained from J. L. Penner (University of Toronto, Toronto, Canada). C. jejuni ATCC33560$^T$, and C. coli ATCC33559$^T$, C. lari and C. upsaliensis were purchased from the American Type Culture Collection. Escherichia coli JM101 [▲-(lac-pro) thi rspL supE endA sbcB hsdR F' traD36 proAB lacI$^g$ Z▲M15] (Maniatis T., Ibid.) and DH5αF'[F'endAl hsdR17(r-$_k$m+$_k$) supE44 thi-1 recAl gyrA relAl θ801acZ-N15 ▲(lacZYA-argF)$_{169}$] were obtained from B. McNeil (University of Toronto), E. coli DR1984 was obtained as described in Sancar, A. et al, J. Bacteriol. 137 (1979) 692–693), and Streptococcus faecalis var. zymogenes was obtained from T. Bleier (University of Toronto). Vectors used were pBR322, and pBlueScript KS-.

Media and growth conditions. C. jejuni and C. coli were grown routinely on Brucella agar base (Difco) supplemented with 5% horse blood in a 5% $CO_2$ incubator at 37° C. E. coli and Streptococcus faecalis were grown in Luria broth at 37° C.

Chemicals. Ampicillin, N-Benzoyl-DL-alanine, Nα-Benzoyl-L-arginine, N-benzoyl-L-glutamic acid, N-Benzoyl-L-glycine, Nα-Benzoyl-L-histidine, N-Benzoyl-DL15 leucine, N-Benzoyl-DL-methionine, N-Benzoyl-DL-phenylalanine, N-Benzoyl-L-threonine, N-Benzoyl-DL-valine were purchased from Sigma Chemical Co. Ninhydrin was purchased from Calbiochem, San Diego, USA. Ferric chloride was purchased from Fisher Scientific Corp., Fair Lawn, N.J., USA. $^{32}$p-dATP, $^{35}$S-dATP, and $^{35}$S-methionine was purchased from ICN. Restriction enzymes were purchased from Boehringer Mannheim, Germany, Gibco-BRL, Mississauga, Canada, and Pharmacia, Upsala, Sweden. Sequencing was performed with the Sequenase kit from United States Biochem. Co., Ohio, USA. Nick-translation was performed using the nick-translation kit from BRL, Mississauga, Canada.

Preparation of crude extracts. C. jejuni ATCC43431, C. coli ATCC33559, Streptococcus faecalis var. zymogenes, E. coli JM101, and E. coli JM101 containing recombinant plasmids were grown overnight in their respective media supplemented with 1% hippuric acid and 50 μg/ml ampicillin where appropriate. Cells were harvested at 12,000×g for 30 min., washed twice in 20 ml 0.85% NaCl, and resuspended in 2 ml 0.15 M potassium phosphate buffer pH 7.4.

The cell suspension was passed through a French press twice at a pressure of 16,000 lbs./sq.in. The extract was cleared of cell envelope by centrifugation 20,000×g for 40 min., and stored frozen at −20° C.

DNA manipulation. Preparation of plasmid DNA from *E. coli* was by rapid alkaline lysis procedure, and digestion with restriction endonucleases, ligation with T4 DNA ligase, transformation with recombinant plasmids, and agarose gel electrophoresis were done as described in Sambrook et al, 1989, supra. Genomic *C. jejuni* DNA was prepared, digested, and blotted as described in Chan et al, Gene 73:185–191, 1988.

Probe preparation and blot hybridization. Plasmid DNA was labelled using a nick-translation kit from Bethesda Research Laboratories (Burlington, Ontario, Canada) using [α-$^{32}$P]dATP. Plasmid restriction fragments were isolated using the GeneCleanII kit. Nick-translated DNA was isolated from unincorporated nucleotides through a Sephadex-G50 spun column. The specific activity of the probes was approximately $1.7 \times 10^7$ dpm/μg DNA. Hybridization was performed as described in Sambrook et al, 1989, supra.

Nucleotide sequencing. The DNA sequence was determined by the dideoxy chain termination method described by Sanger et al. (Sanger et al. PNAS USA, 74:5463, 1977). Small-scale plasmid preparations were obtained by the alkaline lysis procedure (Maniatis, Ibid.) from cells grown overnight in 1.5 ml cultures, and sequenced using the Sequenase kit. Nested deletion clones for sequencing were generated by the method of Henikoff, Gene 28: 351–359, 1984, which is incorporated herein by reference.

Example 1

Isolation, Mapping and Sequencing of Hippuricate Hydrolyzing Clone

A *C. jejuni* genomic library was constructed in pBR322 following the methods of Chan et al (Gene 73: 185–191, 1988). More particularly, *C. jejuni* DNA was isolated from strain TGH9011 (serotype 0:3) for library construction. *C. jejuni* stock cultures were maintained at −70° C. in glycerol salt solutions (40%, v/v, glycerol-3%, w/v, Na3. citrate). Cells were grown on 5% horse blood agar plates with Columbia agar base (Oxoid Ltd., London, U.K.) and incubated for 48 hours at 37° C. in 5% CO2.

*C. jejuni* genomic DNA was isolated and partially digested generally following the procedure described in Maniatis et al, Molecular Cloning, A Laboratory Manual, Cold Spring Harbor Laboratory, Cold Spring Harbor, N.Y. (1982). Partial Sau3A digest conditions which gave the greatest mass of *C. jejuni* DNA fragments in the 4–9 kb range were determined, and large-scale preparation of partially digested DNA (250 μg) was carried out. The reaction was stopped by the addition of EDTA to 20 mM and the tube was placed in ice. After two extractions with phenol-chloroform and ethanol precipitation, the DNA was redissolved in 500 μl TE, loaded on a 10–40% sucrose gradient and centrifuged in a Beckman rotor SW27 at 26000 rev./min for 20 hours at 20° C. Fractions of 0.5 ml were collected and DNA sizes checked on an agarose gel. The 20 appropriate fractions were pooled and dialysed against 4 liters of TE (10 mM Tris-HCl pH 8, 1 mM EDTA). After butanol extraction and ethanol precipitation the DNA was redissolved in TE at 0.5 μg/ml.

Plasmid pBR322 (1 μg) was completely digested with 5 units of BamHI at 37° C. for 200 minutes before the end of the restriction enzyme digest, approximately 6–8 units of calf intestine alkaline phosphatase (Boehringer Mannheim) were added to the digest which was incubated for another 20 minutes at 37° C. The reaction was stopped by heating at 65° C. in the presence of 20 mM EDTA and 0.5% SDS. The DNA was then phenol-extracted, ethanol-precipitated and redissolved in TE to a concentration of 1 μg/μl.

BamHI-cut and dephosphorylated pBR322 (1 μg) was ligated to 0.5 μg of the *C. jejuni* DNA fragments using 1 unit (Weiss) of T4 DNA ligase in the appropriate buffer for 16 hours at 14° C. *E. coli* MM294 was transformed with 100 ng of the ligation mixture by the established procedure detailed in Hanahan, J. Mol. Biol. 166 (1983) 557–580.

The resulting library of $6.3 \times 10^4$ recombinant plasmids was amplified by inoculating the whole culture into 30 ml LB broth containing 50 μg Ap/ml, and after a 10-hour incubation at 37° C. the culture which then had a titer of $2 \times 10^9$ cells/ml was frozen in 50% glycerol in 1 ml aliquots. The number of tetracycline-resistant colonies in this culture was less than 0.2%.

Recombinant plasmids yielding hippurate hydrolysis activity in *E. coli* were isolated from the *C. jejuni* genomic library, prepared as described in Example 1. Clones were screened for hippuricase activity by their ability to catalyze the conversion of N-benzoylglycine to benzoic acid and glycine, the hallmark of hippuricase activity. One thousand five hundred clones were screened in groups of ten to twenty and rescreened using individual colonies. One clone designated pHIPPO containing the putative hippuricase gene was isolated as positive for glycine formation. Further analysis of this clone demonstrated the production of the second product benzoic acid.

The recombinant plasmid pHIPPO was examined by restriction enzyme analysis, and analysis of deletion subclones to determine the location of the region encoding hippuricase activity. DNA was prepared from the recombinant plasmids and analyzed by restriction endonuclease digestion using the restriction enzymes BamHI (B), BglII (G), ClaI (C), EcoRI (E), EcoRV (V), NindIII (H), PstI (P), RsaI (R), SspI (S), XbaI (X), and XhoII (O). There were no restriction enzyme sites for BamHI, EcoRI, EcoRV, or PstI in the insert. The restriction map of recombinant plasmid pHIPPO is shown in FIG. 2.

A 4.0 kb ClaI fragment from pHIPPO was subcloned in both orientations in the ClaI site in pBlueScript, which retained hippuricase activity. Further subclones defined the region encoding hippuricase activity to a 2.7 kb region in the 5.0 kb *C. jejuni* DNA insert. The region was sequenced on both strands. The DNA sequence was determined by the dideoxy chain termination method 5 described by Sanger et al. (Sanger, Supra). Small-scale plasmid preparations were obtained by the alkaline lysis procedure (Maniatis, Supra) from cells grown overnight in 1.5 ml cultures, and sequenced using the Sequenase kit (United States Biochem Co., Ohio, U.S.A.). The region encoding hippuricase activity was sequenced on both strands using the Sequenase kit. The Sequence is shown in SEQ I.D. NO:1 and NO:2 and FIG. 1. The hippuricase gene shows no significant homology to any gene in the GenBank database, nor does the translated polypeptide show similarity to any other protein sequence. The gene is 1.338 kb in size and generates a theoretical product of 446 amino acids with a deduced molecular weight of 50 kd. the ccdon usage of the hippuricase gene is consistent with that of other *Campylobacter jejuni* chromosomal genes 20 sequenced by the inventors.

Deletion mutants for sequencing were constructed using SacI and XbaI in one direction as described by Henikoff, Gene 28: 351–359, 1984.

Southern hybridizations were performed to determine the location of the relevant gene on the specific restriction enzyme fragments used to generate the physical map of *C. jejuni* TGH9011. These include SalI, SmaI, and SacII restriction fragments. *C. jejuni* genomic DNA was digested with the restriction enzymes, and transferred by Vacuum Blot onto GeneScreen nylon membrane (Kim et al, J. Bacteriol 174:3494–3498). A SmaI-HindIII fragment of pHIPPO, containing only hippuricase encoding sequence was labelled with $^{32}$p by nick translation as described above and used to probe the genomic filter containing pulsed-field gel electrophoresis separated fragments of *C. jejuni* genomic DNA. As illustrated in FIGS. 2 and 3, there is only one copy of the gene in *C. jejuni*, and it is located in a region of the chromosome bounded by the SalI A (1,050 kb), SacII A (420 kb) and SmaI A (465 kb) fragments of the physical map shown in FIG. 3. The gene is therefore located within a 420 kb region of the chromosome as are the arg H and rrl genes.

Example 2

Analysis of the protein expressed by the hippuricase gene

Figure 4:
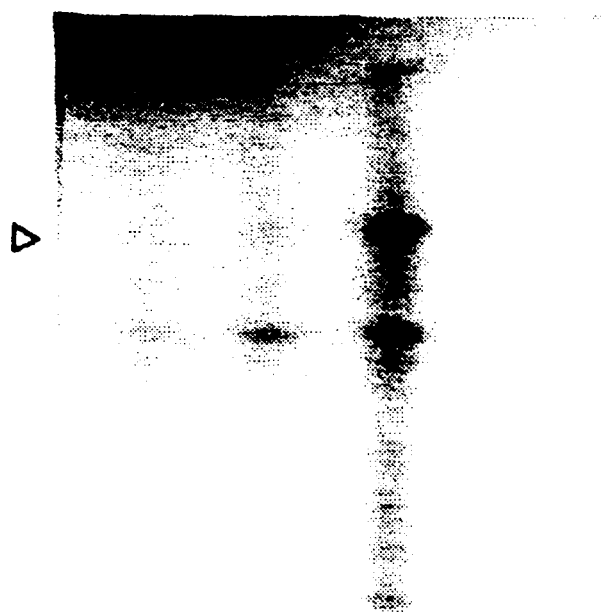
FIG. 4 shows the results of the maxicell analysis of the protein product of the hippuricase gene of he invention.

The protein product of the hippuricase gene was analyzed by maxicell analysis as follows. Plasmid encoded proteins were labelled in W-irradiated *E. coli* DR1984 cells generally as described by Sancar et al (J. Bacteriol. 137:692–693, 1979 and J. Mol. Biol. 148:45–62, 1981). Cells were W-irradiated with a germicidal lamp 15 (15 W) at a height of 50 cm. Survival was between 10–4 and 10–5 following 12–15 h incubation with 200 µg/ml Dcycloserine. Irradiated cells were washed two times with Hershey salts and then labelled with 35S-methionine (40 µCi/ml) for 1 hr in Hershey medium. Cells were lysed by boiling for 3 min. in 50 µl 2×LSB and labelled proteins were separated by 0.1% SDS-13% PAGE as described by Laemmli (1970). After electrophoresis, gels were stained with Coomassie brilliant blue R-250, dried onto 3 MM cellulose paper and then exposed overnight to Kodak XAR-5 film at –70° C. Controls included DR1984 with no plasmid, and DR1984 with pBlueScript. The DR1984 strain showed no proteins produced, the pBlueScript plasmid produced a 30 kD ampicillin resistance determinant. The recombinant plasmid produced the ampicillin resistance determinant, and an additional 42 kD product corresponding to the hippuricase gene product. FIG. 4 shows the results of the maxicell analysis and confirms that the clone is expressed in *E. coli*.

Example 3

Species Specificity of the Hippuricase Protein

The ability of a hippuricase probe, to detect other species of Campylobacter was examined.

An 800 bp SphI/HindIII fragment of plasmid pHIPPO-C/Spl.7 containing the hippuricase encoding sequence (See FIG. 2) was used as a hippuricase-specific probe. Genomic DNAs of hippuricase positive (type-strain) and hippuricase negative strains (5) of *C. jejuni* were digested with HindIII, separated by gel electrophoresis, transferred to GeneScreen, and probed with a radiolabelled probe as described by Maniatis et al (1982, supra).

Figure 5:
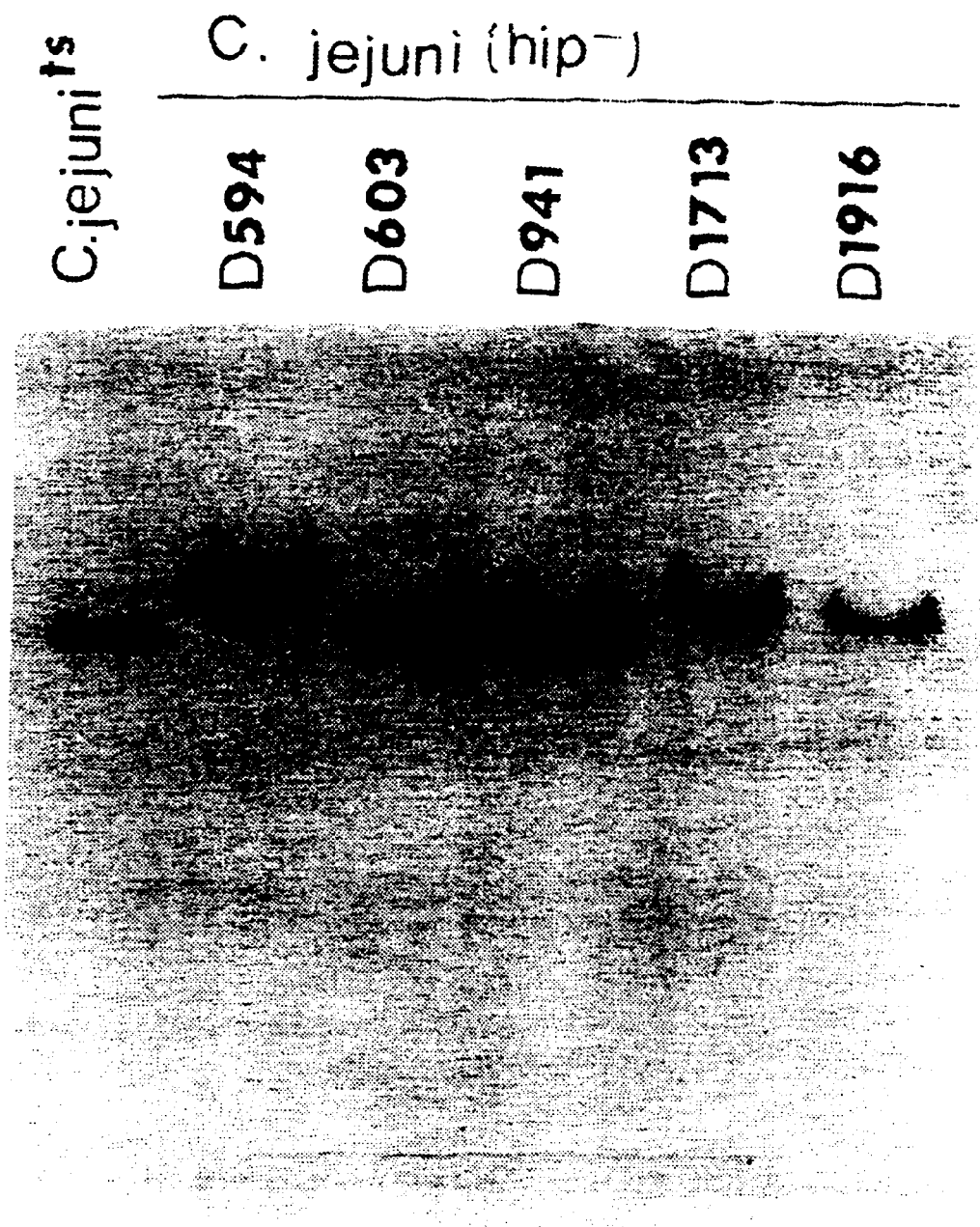
FIG. 5 is a Southern hybridization of chromosomal DNA of hippuricase negative *C. jejuni* isolates.

The hippuricase probe specifically labelled a 2.2 kb HindIII band in the type-strain for *C. jejuni* (lane 1). A single hybridizing band was also observed for all the hippuricase *C. jejuni* isolates (lanes 2–6), ranging in size from 2.2 to 2.4 kb in size. Therefore, all the *C. jejuni* strains contained the hippuricase gene sequences, even if they were biochemically negative (FIG. 5). One of the HindIII sites is located within the hippuricase gene, but the second is located upstream of the hippuricase gene. This results in a polymorphic banding pattern using this restriction enzyme. Southern hybridization is being performed using Sau3A digested chromosomal DNA which should generate a common 670 bp fragment.

Figure 6:
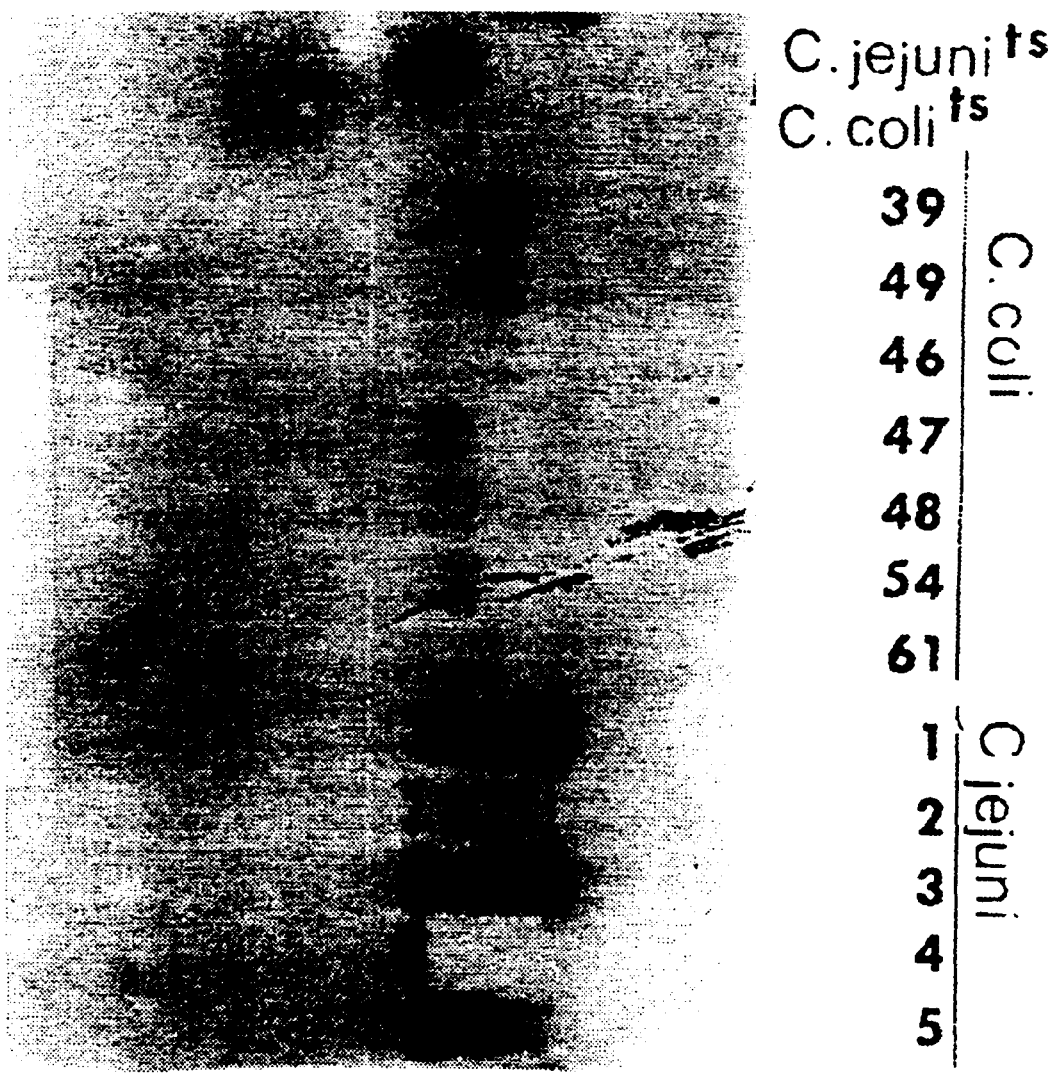
FIG. 6 is a Southern hybridization of chromosomal DNA of *C. coli* and *C. jejuni* isolates.

The same probe was used to screen various *C. jejuni* and *C. coli* isolates using the method described above. Some of the isolates were type strains and some were classified using conventional methods of biochemical reactions etc. As shown in FIG. 6, the type-strain for *C. jejuni* was positive (lane 1), generating a 2.2kb HindIII hybridizing band. The type-strain for *C. coli* was negative, even under low stringency conditions (25 C, 2×SSC) of hybridization. All the *C. jejuni* strains gave a positive hybridizing signal with the hippuricase probe (lanes 10–14), and were positive in the biochemical test. Seven *C. coli* isolates, which were not type strains, gave a weak hybridizing signal using a *C. jejuni* hippuricase-specific probe at high stringency (65 C, 0.2× SSC) (FIG. 6). These isolates were all negative in the hippuricase biochemical test and were incorrectly identified as *C. coli*.

Example 4

Demonstration of Hippuricase in Cell-free Extracts

Crude cell-free extracts were prepared from the recombinants and hippuricase activity was measured. More particularly, *C. jejuni* ATCC43431, *C. coli* ATCC33559, *Streptococcus faecalis* var. *zymogenes*, *E. coli* JM101, and *E. coli* JM101 containing recombinant plasmids were grown overnight in their respective media supplemented with 1% hippuric acid and 50 llg/ml ampicillin where appropriate. Cells were harvested at 12,000×g for 30 min., washed twice in 20 ml 0.85% NaCl, and resuspended in 2 ml 0.15 M potassium phosphate buffer pH 7.4 . The cell suspension was passed through a French press twice at a pressure of 16,000 lbs./sq.in. The extract was cleared of cell envelope by centrifugation at 20,000×g for 40 min., and stored frozen at –20° C.

Enzyme activity in the crude cell free extracts was determined as follows. Hydrolytic activity towards N-benzoylamino-acid was that estimated by the procedure of Kameda et al. (Chem. Pharm. Bull. Tokyo 16:1023, 1968). The reaction mixture contained 1 ml of 10 mM N-benzoylamino-acid, 0.5 ml of 0.1 M Tris buffer (pH 8.0), and 0.5 ml of appropriately diluted enzyme solution. Incubation was at 37° C. for 0, 10, and 20 min., after which 0.2 ml was removed and boiled for 2 min. to eliminate enzyme activity. A 0.1 ml aliquot of ninhydrin reagent (3.5% in a 1:1 solution of acetone/butanol) was added, and boiled for 20 min. The solution was diluted with 60% ethanol, and the absorption intensity was measured at 570 nm relative to the amino acid standard. The enzyme activity is expressed in terms of micromoles of liberated amino acid per hr. per mg protein under the above conditions. Protein content of the enzyme solution was measured by the method of Lowry et al., J. Biol. Chem. 193, 265–275, 1951, which is incorporated herein by reference, using bovine serum albumin as the standard.

Hippuricase activity was detected by the following methods: (1) One ml of overnight culture was centrifuged at 12000×g for 2 min. at room temperature, as were all subsequent centrifugations. The bacterial pellet was washed in a 1% aqueous solution of sodium hippurate pH 7.2, recentrifuged, and resuspended in 100 µl of 1% aqueous sodium hippurate. The cells were incubated at 37 C for 1 hr. and pelleted. The supernatant was transferred to a 96 well microtitre plate and assayed for the presence of glycine by the addition of 50 μl ninhydrin reagent (3.5% in 1:1 acetone/butanol) according to the method of Hwang and Ederer (J. Clin. Microbiol. 1:114, 1975). (2) Benzoic acid was detected using the procedure described by Facklam et al. (Appl. Microbiol. 27:107, 1974). After overnight growth in Luria broth supplemented with 1% hippurate, the cells were centrifuged, and 0.8 ml of the clarified supernatant was mixed with 0.2 ml acidified FeC13, and the presence of a large brown precipitate was considered positive; (3) Alkaline reaction was detected in phenol-red hippurate agar slants as proposed by Thirst (J. Gen. Microbiol. 17:390, 1957). The media contains casamino acids, 1.0 g; yeast extract, 1.0 g; $K_2HPO_4$, 10 mM; NaCl, 5.0 g; sodium hippurate, 10 g; phenol red (1.6% solution), 2 ml; agar, 13 g; distilled water, 1 liter. Positive controls in each assay were *Streptococcus faecalis* var. *zymogenes*, and *Campylobacter jejuni*. Negative controls were uninoculated broth cultures, *E. coli* JM101, *E. coli* MM294, and *Campylobacter coli*.

The enzyme was detectable in *C. jejuni* and *Streptococcus faecalis* var. *zymogenes*, but not in *E. coli* or *C. coli*. Hippuricase activity was linear with respect to protein concentration and time, indicating that the protein functions as an enzyme. The results also confirm that hippuricase activity is not associated with the cell wall or cell membrane fraction of the bacterial organism. The *C. jejuni* protein was not denatured by incubation at 65° C., but was inactivated at 100° C. after a two minute 35 exposure.

The results show that the genetic locus encoding hippuricase is specific for *C. jejuni*, but is not detectable by enzymatic or DNA hybridization (see Example 3) in any other species of Campylobacter. Hippuricase activity is present in *S. faecalis* var. *zymogenes*, however, the probe (See Example 3) is unable to detect 5 hippuricase sequences form this organism Example 5

Substrate specificity of the recombinant hippuricase protein

Substrate specificity of the recombinant hippuricase protein was compared to that of the protein from the cell extract of *C. jejuni*. The recombinant hippuricase showed greatest activity in benzoyl(bz-)glycine and bz-histidine, whereas the cell extract *C. jejuni* hippuricase had greatest activity with bz-leucine and bz-methionine. The recombinant protein did not show any activity with bz-arginine, in contrast to the weak reaction with the cell extract from *C. jejuni*.

Example 6

The glutathione S-transferase gene fusion system is an integrated system for the expression, purification, and detection of fusion proteins produced in *E. coli*. The vectors offer a tac promoter for chemically inducible, high-level expression; an internal lac Iq gene for use in any *E. coli* host; mild elution conditions for release of fusion proteins from the affinity matrix, thus minimizing effects on antigenicity and functional activity; and thrombin cleavage recognition sites for cleaving the desired protein from the fusion product.

A fusion of the hippuricase gene was constructed into this vector by ligation of an XmnI restriction enzyme fragment containing the carboxy-terminal portion of the gene into the SmaI restriction site in the vector. The reading frame of hippuricase is maintained with respect to GST. Forty-seven nucleotides upstream of the XmnI restriction enzyme site and without the coding sequence from hippuricase were deleted in this construct. This represents a loss of only sixteen amino-terminal amino-acid residues from the native polypeptides, which should not interfere with the production of antibodies to the hippuricase protein. The construct has the following characteristics at the fusion junction:

```
                    Thombin cleavage site
... CTG GTT CCG CGT
... Leu Val Pro Arg
GST
                    GGA TCC CAA TTC GTC ATC AAA TTC...
                    Gly Ser Gln Phe Val Ile Lys Phe...
                    Hippuricase
```

These sequences were confirmed by dideoxynucleotide sequencing of the junction region using a synthetic oligonucleotide primer designed specifically for this purpose.

The production of a fusion protein of the expected size was demonstrated for a GST-hippuricase protein in whole cell extracts of *E. coli* induced with IPTG. The GST-hippuricase protein was purified to homogeneity by using a Glutathione Sepharose affinity matrix to separate the fusion protein from total cellular protein, and by elution of the fusion protein using reduced glutathione.

The hippuricase protein can be removed from the GST affinity handle by cleavage of the fusion protein with thrombin, followed by removal of the GST moiety using the Glutathione Sepharose system used to initially isolate the fusion protein from total protein.

Legend for FIG. 3

Location of the hippuricase gene on the physical map of *C. jejuni* strain TGH9011 with respect to other genetic markers isolated from this organism. The 1812 kb genome is divided into quartiles using rrnA as the zero-reference point. Genes which have been mapped onto the chromosome arc listed below.

| Gene symbol | Phenotypic trait |
| --- | --- |
| hipO | Hippuricase |
| rrlA | 23S rRNA of rrnA operon |
| rrsA | 16S rRNA of rrnA operon |
| rrlB | 23S rRNA of rrnB operon |
| rrsB | 16S rRNA of rrnB operon |
| rrlC | 23S rRNA of rrnC operon |
| rrsC | 16S rRNA of rrnC operon |
| argA | NAc-glutamate synthetase |
| argB | NAc-glutamate kinase |
| argC | NAc-glutamylphosphate reductase |
| argD | Acetylornithine aminotransferase |
| argE | Acetylornithase |
| argF | Ornithine caramoyltransferase |
| argH | Argininosuccinate lyase |
| fla1 fla2 | Flagellin |
| glyA | Serine hydroxymethyltransferase |
| lysS | Lysyl tRNA sythetase |
| proA | Glutamylphosphate reductase |
| flgG | Flagellin-associated protein |

Legend for FIG. 4

Maxicell analysis of hippuricase-encoding plasmids. Plasmid encoded proteins were labelled in UV-irradiated *E. coli* DR1984 cells as described by Sancar et al. (1979, 1981). Cells were UV-irradiated with a germicidal lamp (15 W) at a height of 50 cm. Survival was between $10^{-4}$ and $10^{-4}$ following 12–15 h incubation with 200 μg/ml D-cycloserine. Irradiated cells were washed two times with Hershey salts and then labelled with 35S-methionine (40 μCi/ml) for 1 h in Hershey medium. Cells were lysed by boiling for 3 min in 50 μl 2×LSB and labelled proteins were separated by 0.1% SDS-13% PAGE as described by Laemmli (1970). After electrophoresis, gels were stained with Coomassic brilliant blue R-250, dried onto 3 MM cellulose paper and then exposed to Kodak XAR-5 film at −70° C. *E. coli* control cells containing no plasmid produced no radioactively labelled proteins. Cells containing plasmid pBR322 produced a single protein of molecular weight 31 kd, corresponding to the ampicillin resistance determinant. Cells containing plasmid pHIPO produced both a 31 kd protein and a 42 kd protein corresponding to the hippuricase polypeptide product.

Legend for FIG. 5

Southern hybrdization of chromosomal DNA of hippuricase-negative isolates of *Campylobacter jejuni*.

Genomic DNA was prepared from five strains of *C. jejuni* which were shown to be hippuricase negative in the standard biochemical test, and the type-strain for *C. jejuni* which is hippuricase positive. The DNA was digested with HindIII. The fragments were separated by gel electrophoresis, transferred to GeneScreen, and probed with a radiolabelled 800 bp kb SphI/HindIII fragment of pHIP-C/Spl.7 as described by Maniatis et al. (1982).

The hippuricase probe specifically labelled a 2.2 kb HindIII band in the type strain for *C. jejuni* (lane 1). A single hybridizing band was also observed for all the hippuricase negative *C. jejuni* isolates (lanes 2–6), ranging in size from 2.2 to 2.4 kb in size. The polymorphic nature of the hybridizing pattern is a result of the fact that one of the HindIII sites is not within the encoding sequence of the hippuricase gene.

Legend for FIG. 6

Southern hybrdization of chromosomal DNA of *Campylobacter coli* and *Campylobacter jejuni* isolates.

Genomic DNA was prepared from the type-strains of *C. jejuni*, and *C. coli*, and from strains corresponding to serotype-reference strains. The DNA was digested with HindIII. The fragments were separated by gel electrophoresis, transferred to GeneScreen, and probed with a radiolabelled 800 bp kb SphI/HindIII fragment of pHIP-C/Spl.7 as described by Maniatis et al. (1982).

The hippuricase probe specifically labelled a 2.2 kb HindIII band in the type strain for *C. jejuni* (lane 1), but did not detect any hybridizing band in *C. coli*, even at low stringency (25 C, 2×SSC). All *C. jejuni* strains hybridized to the hippuricase probe (lanes 10–14). All *C. coli* serotype reference strains also hybridized to the hippuricase probe at high stringency (65 C, 0.2×SSC), although they generated a weaker signal.

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1338 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..1338

(xi) SEQUENCE DESCRIPTION: SEQ ID NO:1:

```
ATG AGT GAC TTT TGG AGA ATA CCT TTG TTA TAC TAT CAT TTA ACC ATG        48
Met Ser Asp Phe Trp Arg Ile Pro Leu Leu Tyr Tyr His Leu Thr Met
 1               5                  10                  15

GGT AGT AAA TCT TGG AGT GTT GAT AAA ACC CAT AGA TTT ACT TTG GGT        96
Gly Ser Lys Ser Trp Ser Val Asp Lys Thr His Arg Phe Thr Leu Gly
             20                  25                  30

TTT GTT TAT ATT TTT GCT TTG ATT TTT ATT TCA GCG ATC TTA GCA CAA       144
Phe Val Tyr Ile Phe Ala Leu Ile Phe Ile Ser Ala Ile Leu Ala Gln
         35                  40                  45

TTT GTT TTA CCT AGA AGA GAA AAT TTA TAC AAG GAG AAA AAT AGA TTG       192
Phe Val Leu Pro Arg Arg Glu Asn Leu Tyr Lys Glu Lys Asn Arg Leu
     50                  55                  60

AAT TTA ATT CCA GAA ATA CTA GAC TTA CAA GGC GAA TTT GAA AAA ATT       240
Asn Leu Ile Pro Glu Ile Leu Asp Leu Gln Gly Glu Phe Glu Lys Ile
 65                  70                  75                  80

CGT CAT CAA ATT CAT GAA AAT CCT GAG CTT GGT TTT GAT GAA TTA TGT       288
```

```
              Arg His Gln Ile His Glu Asn Pro Glu Leu Gly Phe Asp Glu Leu Cys
                          85                  90                  95

ACT GCA AAA TTA GTG GCG CAA AAA TTA AAA GAA TTT GGT TAT GAG GTT              336
Thr Ala Lys Leu Val Ala Gln Lys Leu Lys Glu Phe Gly Tyr Glu Val
            100                 105                 110

TAT GAG GAA ATA GGA AAA ACA GGC GTT GTG GGG GTT TTA AAA AGG GGA              384
Tyr Glu Glu Ile Gly Lys Thr Gly Val Val Gly Val Leu Lys Arg Gly
            115                 120                 125

ATA GCG ATT AAA AAA ATA GGA CTC GTG CAG ATA TGG AAT GCT TTG CCT              432
Ile Ala Ile Lys Lys Ile Gly Leu Val Gln Ile Trp Asn Ala Leu Pro
130                 135                 140

TTG CAA GAA TGC ACA AAT TTG CCT TAT AAA AGC AAA AAA GAA AAT GTA              480
Leu Gln Glu Cys Thr Asn Leu Pro Tyr Lys Ser Lys Lys Glu Asn Val
145                 150                 155                 160

ATG CAT GCT TGC GGT CAT GAT GGA CAT ACT ACT TCT TTA TTG CTT GCT              528
Met His Ala Cys Gly His Asp Gly His Thr Thr Ser Leu Leu Leu Ala
                165                 170                 175

GCA AAG TAT TTA GCA AGT CAG AAT TTT AAT GGC ACT TTA AAT CTT TAT              576
Ala Lys Tyr Leu Ala Ser Gln Asn Phe Asn Gly Thr Leu Asn Leu Tyr
            180                 185                 190

TTT CAA CCT GCT GAA GAG GGT TTG GGT GGT GCT AAG GCA ATG ATA GAA              624
Phe Gln Pro Ala Glu Glu Gly Leu Gly Gly Ala Lys Ala Met Ile Glu
            195                 200                 205

GAT GGA TTG TTT GAA AAA TTT GAT AGT GAT TAT GTT TTT GGA TGG CAC              672
Asp Gly Leu Phe Glu Lys Phe Asp Ser Asp Tyr Val Phe Gly Trp His
210                 215                 220

AAT ATG CCT TTT GGT AGC GAT AAG AAA TTT TAT CTT AAA AAA GGT GCG              720
Asn Met Pro Phe Gly Ser Asp Lys Lys Phe Tyr Leu Lys Lys Gly Ala
225                 230                 235                 240

ATG ATG GCT TCT TCG GAT AGT TAT AGC ATT GAA GTT ATT GGA AGA GGT              768
Met Met Ala Ser Ser Asp Ser Tyr Ser Ile Glu Val Ile Gly Arg Gly
                245                 250                 255

GGT CAT GCA AGT GCT CCA AAA AAA ATA ACA GAT CCT ATT TAT GCT GCT              816
Gly His Ala Ser Ala Pro Lys Lys Ile Thr Asp Pro Ile Tyr Ala Ala
            260                 265                 270

TCT TTA CTT ATT GTA ACT TTA CAA AGC ATA GTA TCT TGC AAT GTT GAT              864
Ser Leu Leu Ile Val Thr Leu Gln Ser Ile Val Ser Cys Asn Val Asp
            275                 280                 285

CCC CAA AAT TCA GCA GTT GTA AGC ATA GGA GCT TTT AAT GCT GGA CAT              912
Pro Gln Asn Ser Ala Val Val Ser Ile Gly Ala Phe Asn Ala Gly His
290                 295                 300

GCT TTT AAT ATC ATT CCA GAT ATT GTA ACG ATT AAA ATG AGT GTT AGA              960
Ala Phe Asn Ile Ile Pro Asp Ile Val Thr Ile Lys Met Ser Val Arg
305                 310                 315                 320

GGA TTA GAT AAT GAA ACT AGA AAG CTA ACT GAA GAA AAA AAA AAT AAA             1008
Gly Leu Asp Asn Glu Thr Arg Lys Leu Thr Glu Glu Lys Lys Asn Lys
                325                 330                 335

ATT TGT AAA GGT CTT GCA CAG GCT AAT GAT ATA GAG ATT AAA ATC AAT             1056
Ile Cys Lys Gly Leu Ala Gln Ala Asn Asp Ile Glu Ile Lys Ile Asn
            340                 345                 350

AAA AAT GTT GTT GCA CCA GTG ACT ATG AAT AAC GAT GAA GCT GTG GAT             1104
Lys Asn Val Val Ala Pro Val Thr Met Asn Asn Asp Glu Ala Val Asp
            355                 360                 365

TTT GCT AGT GAG GTT GCA AAA GAA TTA TTT GGC GAA AAA AAT TGT GAA             1152
Phe Ala Ser Glu Val Ala Lys Glu Leu Phe Gly Glu Lys Asn Cys Glu
370                 375                 380

TTT AAT CAT CGT CCT TTA ATG GCA AGT GAG GAT TTT GGA TTT TTT TAC             1200
Phe Asn His Arg Pro Leu Met Ala Ser Glu Asp Phe Gly Phe Phe Tyr
385                 390                 395                 400

GAA ATG AAA AAA TGT GCC TAT GCT TTT TTA GAA AAT GAA AAC GAC ATT             1248
```

```
Glu Met Lys Lys Cys Ala Tyr Ala Phe Leu Glu Asn Glu Asn Asp Ile
            405                 410                 415

TAT TTA CAT AAT TCT AGT TAT GTT TTT AAT GAT AAG CTT TTA GCT AGG         1296
Tyr Leu His Asn Ser Ser Tyr Val Phe Asn Asp Lys Leu Leu Ala Arg
            420                 425                 430

GCT GCA AGT TAT TAT GCG AAG CTA GCT TTA AAA TAC TTA AAA                 1338
Ala Ala Ser Tyr Tyr Ala Lys Leu Ala Leu Lys Tyr Leu Lys
            435                 440                 445
```

(2) INFORMATION FOR SEQ ID NO:2:

(i) SEQUENCE CHARACTERISTICS:
        (A) LENGTH: 446 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Asp Phe Trp Arg Ile Pro Leu Leu Tyr Tyr His Leu Thr Met
 1               5                  10                  15

Gly Ser Lys Ser Trp Ser Val Asp Lys Thr His Arg Phe Thr Leu Gly
            20                  25                  30

Phe Val Tyr Ile Phe Ala Leu Ile Phe Ile Ser Ala Ile Leu Ala Gln
            35                  40                  45

Phe Val Leu Pro Arg Arg Glu Asn Leu Tyr Lys Glu Lys Asn Arg Leu
 50                  55                  60

Asn Leu Ile Pro Glu Ile Leu Asp Leu Gln Gly Glu Phe Glu Lys Ile
 65                  70                  75                  80

Arg His Gln Ile His Glu Asn Pro Glu Leu Gly Phe Asp Glu Leu Cys
            85                  90                  95

Thr Ala Lys Leu Val Ala Gln Lys Leu Lys Glu Phe Gly Tyr Glu Val
            100                 105                 110

Tyr Glu Glu Ile Gly Lys Thr Gly Val Val Gly Val Leu Lys Arg Gly
            115                 120                 125

Ile Ala Ile Lys Lys Ile Gly Leu Val Gln Ile Trp Asn Ala Leu Pro
130                 135                 140

Leu Gln Glu Cys Thr Asn Leu Pro Tyr Lys Ser Lys Lys Glu Asn Val
145                 150                 155                 160

Met His Ala Cys Gly His Asp Gly His Thr Thr Ser Leu Leu Leu Ala
            165                 170                 175

Ala Lys Tyr Leu Ala Ser Gln Asn Phe Asn Gly Thr Leu Asn Leu Tyr
            180                 185                 190

Phe Gln Pro Ala Glu Glu Gly Leu Gly Gly Ala Lys Ala Met Ile Glu
            195                 200                 205

Asp Gly Leu Phe Glu Lys Phe Asp Ser Asp Tyr Val Phe Gly Trp His
            210                 215                 220

Asn Met Pro Phe Gly Ser Asp Lys Lys Phe Tyr Leu Lys Lys Gly Ala
225                 230                 235                 240

Met Met Ala Ser Ser Asp Ser Tyr Ser Ile Glu Val Ile Gly Arg Gly
            245                 250                 255

Gly His Ala Ser Ala Pro Lys Lys Ile Thr Asp Pro Ile Tyr Ala Ala
            260                 265                 270

Ser Leu Leu Ile Val Thr Leu Gln Ser Ile Val Ser Cys Asn Val Asp
            275                 280                 285

Pro Gln Asn Ser Ala Val Val Ser Ile Gly Ala Phe Asn Ala Gly His
            290                 295                 300
```

-continued

```
Ala Phe Asn Ile Ile Pro Asp Ile Val Thr Ile Lys Met Ser Val Arg
305                 310